US007345153B2

(12) United States Patent
Litwin et al.

(10) Patent No.: US 7,345,153 B2
(45) Date of Patent: Mar. 18, 2008

(54) COMPOUNDS CAPABLE OF INHIBITING HIV-1 INFECTION

(75) Inventors: Virginia M. Litwin, Fayetteville, NY (US); Graham P. Allaway, Wilmslow (GB); Paul J. Maddon, New York, NY (US)

(73) Assignee: Progenics Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 11/544,346

(22) Filed: Oct. 5, 2006

(65) Prior Publication Data

US 2007/0025983 A1    Feb. 1, 2007

Related U.S. Application Data

(63) Continuation of application No. 09/891,062, filed on Jun. 25, 2001, now Pat. No. 7,118,859, which is a continuation of application No. 09/118,415, filed on Jul. 17, 1998, now abandoned, which is a continuation of application No. PCT/US97/00758, filed on Jan. 17, 1997, which is a continuation-in-part of application No. 08/587,458, filed on Jan. 17, 1996, now abandoned.

(51) Int. Cl.
     *C07K 16/00*      (2006.01)
(52) U.S. Cl. ............................. 530/388.73; 530/388.73
(58) Field of Classification Search ............ 530/388.73
See application file for complete search history.

(56) References Cited

U.S. PATENT DOCUMENTS

| | | | |
|---|---|---|---|
| 4,886,743 A | 12/1989 | Hood | |
| 5,021,409 A | 6/1991 | Murrer et al. | |
| 5,071,964 A | 12/1991 | Dustin et al. | |
| 5,091,513 A | 2/1992 | Huston et al. | |
| 5,126,433 A | 6/1992 | Maddon et al. | |
| 5,215,913 A | 6/1993 | Posner | |
| 5,225,539 A | 7/1993 | Winter et al. | |
| 5,440,021 A | 8/1995 | Chuntharapai et al. | |
| 5,449,608 A | 9/1995 | Young et al. | |
| 5,504,003 A | 4/1996 | Li et al. | |
| 5,603,933 A | 2/1997 | Dwyer et al. | |
| 5,668,149 A | 9/1997 | Oroszlan et al. | |
| 5,817,767 A | 10/1998 | Allaway | |
| 5,854,400 A | 12/1998 | Chang et al. | |
| 5,939,320 A | 8/1999 | Littman et al. | |
| 5,994,515 A | 11/1999 | Hoxie et al. | |
| 6,025,154 A | 2/2000 | Li et al. | |
| 6,100,087 A | 8/2000 | Rossi et al. | |
| 6,107,019 A | 8/2000 | Allaway et al. | |
| 6,258,527 B1 | 7/2001 | Littman et al. | |
| 6,258,782 B1 | 7/2001 | Barney et al. | |
| 6,261,763 B1 | 7/2001 | Allaway et al. | |
| 6,265,184 B1 | 7/2001 | Gray et al. | |
| 6,268,477 B1 | 7/2001 | Gray et al. | |
| 6,344,545 B1 | 2/2002 | Allaway et al. | |
| 6,448,375 B1 | 9/2002 | Samson | |
| 6,511,826 B2 | 1/2003 | Li et al. | |
| 7,175,988 B2 | 2/2003 | Roschke et al. | |
| 6,528,625 B1 | 3/2003 | Wu et al. | |
| 6,548,636 B2 | 4/2003 | Dragic | |
| 6,692,938 B2 | 2/2004 | Samson et al. | |
| 6,743,594 B1 | 6/2004 | Li | |
| 6,759,519 B2 | 7/2004 | Li et al. | |
| 6,797,811 B1 | 9/2004 | Gray et al. | |
| 6,800,447 B2 | 10/2004 | Samson | |
| 6,800,729 B2 | 10/2004 | Li et al. | |
| 6,908,734 B2 | 6/2005 | Dragic et al. | |
| 6,930,174 B2 | 8/2005 | Samson et al. | |
| 6,972,126 B2 | 12/2005 | Allaway et al. | |
| 7,060,273 B2 | 6/2006 | Olson et al. | |
| 7,118,859 B2 | 10/2006 | Litwin et al. | |
| 7,122,185 B2 | 10/2006 | Olson et al. | |
| 7,129,055 B2 | 10/2006 | Littman et al. | |
| 7,138,119 B2 | 11/2006 | Olson et al. | |
| 2001/0000241 A1 | 4/2001 | Li et al. | |

(Continued)

FOREIGN PATENT DOCUMENTS

CA      2216990      12/1997

(Continued)

OTHER PUBLICATIONS

Abaza, M.S.I et al., (1992) "Effects of Amino Acid Substitutions Outside An Antigenic Site On Protein Binding To Monoclonal Antibodies Of Predetermined Specificity Obtained By Peptide Immunization: Demonstration With Region 94-100 (Antigenic Site 3) Of Myoglobin", *J. Prot. Chem.* 11:433-443.
Alexander, H. et al., (1992) "Altering The Antigenicity Of Proteins", *Proc. Natl. Acad. Sci.* 89:3352-3356.
Ashorn, P.A. et al., (1990) "Human Immunodeficiency Virus Envelope Glycoprotein/CD4 Mediated Fusion Of Nonprimate Cells With Human Cells", *J. Virol.* 64:2149-2156.
Attanasio, R. et al., (1991) "Anti-Idiotypic Antibody Response To Monoclonal Anti-CD4 Preparations In Nonhuman Primate Species", *J. Immunol.* 146:507-514.
Brenner, T.J. et al., (1996) "Relation Between HIV-1 Syncytium Inhibition Antibodies And Clinical Outcome In Children", *Lancet* 337:1001-1005.

(Continued)

*Primary Examiner*—Jeffrey S. Parkin
(74) *Attorney, Agent, or Firm*—John P. White; Cooper & Dunham LLP

(57) ABSTRACT

This invention provides an antibody capable of specifically inhibiting the fusion of an HIV-1 envelope glycoprotein$^+$ cell with an appropriate CD4$^+$ cell without cross reacting with the HIV-1 envelope glycoprotein or CD4 and capable of inhibiting infection by one or more strains of HIV-1. This antibody is then used to identify a molecule which is important for HIV infection. Different uses of the antibody and the molecule are described.

7 Claims, 8 Drawing Sheets

U.S. PATENT DOCUMENTS

| | | |
|---|---|---|
| 2001/0046512 A1 | 11/2001 | Litwin et al. |
| 2002/0045161 A1 | 4/2002 | Allaway et al. |
| 2002/0048786 A1 | 4/2002 | Rosen et al. |
| 2002/0061834 A1 | 5/2002 | Rosen et al. |
| 2002/0068813 A1 | 6/2002 | Dragic et al. |
| 2002/0146415 A1 | 10/2002 | Olson et al. |
| 2002/0150888 A1 | 10/2002 | Gray et al. |
| 2002/0155429 A1 | 10/2002 | Allaway et al. |
| 2003/0003440 A1 | 1/2003 | Lopalco et al. |
| 2003/0023044 A1 | 1/2003 | Li et al. |
| 2003/0092632 A1 | 5/2003 | Dragic et al. |
| 2003/0166024 A1 | 9/2003 | Rosen et al. |
| 2003/0166870 A1 | 9/2003 | Wu et al. |
| 2003/0195348 A1 | 10/2003 | Combadiere et al. |
| 2004/0062767 A1 | 4/2004 | Olson et al. |
| 2004/0086528 A1 | 5/2004 | Allaway et al. |
| 2004/0110127 A1 | 6/2004 | Samson et al. |
| 2004/0151719 A1 | 8/2004 | Li et al. |
| 2004/0161739 A1 | 8/2004 | Samson et al. |
| 2004/0228869 A1 | 11/2004 | Olson et al. |
| 2004/0230037 A1 | 11/2004 | Gray et al. |
| 2004/0259785 A1 | 12/2004 | Combadiere et al. |
| 2005/0118677 A1 | 6/2005 | Combadiere et al. |
| 2005/0154193 A1 | 7/2005 | Roschke et al. |
| 2005/0260565 A1 | 11/2005 | Gray et al. |
| 2006/0029932 A1 | 2/2006 | Allaway et al. |
| 2006/0140977 A1 | 6/2006 | Allaway et al. |
| 2006/0194244 A1 | 8/2006 | Allaway et al. |
| 2006/0233798 A1 | 10/2006 | Olson et al. |
| 2007/0026441 A1 | 2/2007 | Olson et al. |

FOREIGN PATENT DOCUMENTS

| | | |
|---|---|---|
| EP | 96870021.1 | 3/1996 |
| EP | 96870102.9 | 8/1996 |
| EP | 0815137 | 12/1996 |
| EP | 1145721 A2 | 10/2001 |
| EP | 1146055 A2 | 10/2001 |
| EP | 1146122 A2 | 10/2001 |
| EP | 1148126 A2 | 10/2001 |
| EP | 1148127 A2 | 10/2001 |
| EP | 1149582 A2 | 10/2001 |
| EP | 1199360 A2 | 4/2002 |
| EP | 0883687 B1 | 10/2004 |
| EP | 1482042 A1 | 12/2004 |
| WO | WO92/01451 | 2/1992 |
| WO | WO94/22477 | 10/1994 |
| WO | WO95/16789 | 6/1995 |
| WO | WO96/39437 | 12/1996 |
| WO | WO96/41020 | 12/1996 |
| WO | WO97/22698 | 6/1997 |
| WO | WO97/26009 | 7/1997 |
| WO | WO97/28258 | 8/1997 |
| WO | WO97/032019 | 9/1997 |
| WO | WO97/37005 | 10/1997 |
| WO | WO97/44055 | 11/1997 |
| WO | WO 97/44462 | 11/1997 |
| WO | WO97/45543 | 12/1997 |
| WO | WO97/47318 | 12/1997 |
| WO | WO97/47319 | 12/1997 |
| WO | WO97/49424 | 12/1997 |
| WO | WO98/18826 | 5/1998 |
| WO | WO 98/56421 | 12/1998 |
| WO | WO 00/35409 | 6/2000 |
| WO | WO 01/55439 | 8/2001 |
| WO | WO 01/58915 | 8/2001 |
| WO | WO 01/58916 | 8/2001 |
| WO | WO 01/64710 | 9/2001 |
| WO | WO 02/22077 | 3/2002 |
| WO | WO 02/064612 | 8/2002 |
| WO | WO 02/068608 | 9/2002 |
| WO | WO 02/083172 | 10/2002 |
| WO | WO 03/072766 | 9/2003 |
| WO | WO 07/014114 | 2/2007 |

OTHER PUBLICATIONS

Broder, C.C. et al., (1993) "The Block To HIV-1 Envelope Glycoprotein-Mediated Membrane Fusion In Animal Cells Expressing Human CD4 Can Be Overcome By A Human Cell Component (s)", *Virol.* 193:483-491.

Busso, M. et al., (1991) "HIV-Induced Syncytium Formation Requires The Formation Of Conjugates Between Virus-Infected And Uninfected T-Cells In Vitro", *AIDS* 5:1425-1432.

Clapham, P.R. et al., (1991) "Specific Cell Surface Requirements For The Infection Of CD4-Positive Cells By Human Immunodeficiency Virus Types 1 And 2 By Simian Immunodeficiency Virus", *Virol.* 181:703-715.

Dalgleish, A.G., (1995) "HIV And CD26", *Nat. Med.* 1:881-882.

Dragic, T. et al., (1992) "Complementation Of Murine Cells For Human Immunodeficiency Virus Envelope/CD4-Mediated Fusion In Human/ Murine Heterokaryons", *J. Virol.* 66:4794-4802.

Dragic, T.V. et al., (1995) "Proteinase-Resistant Factors In Human Erythrocyte Membranes Mediate CD-4 Dependent Fusion With Cells Expressing Human Immunodeficiency Virus Type 1 Envelope Glycoproteins", *J. Virol.* 69:1013-1018.

Golding, H. et al., (1992) "LFA-1 Adhesion Molecules Are Not Involved In The Early Stages Of HIV-1 env-Mediated Cell Membrane Fusion", *AIDS Res. Hum. Retroviruses* 8:1593-1598.

Harrington, R.D. And Geballe, A.P., (1993) "Cofactor Requirement For Human Immunodeficiency Virus Type 1 Entry Into A CD4-Expressing Human Cell Line", *J. Virol.* 67:5939-5947.

Hattori, T. et al., (1989) "Involvement Of Tryptase-Related Cellular Protease(s) In Human Immunodeficiency Virus Type 1 Infection", *FEBS Letters* 248:48-52.

Hildreth, J.E. et al., (1989) "Involvement Of A Leukocyte Adhesion Receptor (LFA-1) In HIV-Induced Syncytium Formation" *Science* 244:1075-1078.

Jacobson, J.M. et al., (1993) "Passive Immunotherapy In The Treatment Of Advanced Human Immunodeficiency Virus Infection", *J. Infect. Dis.* 168:298-305.

Karwowska, S. et al., (1991) "Passive Immunization For The Treatment And Prevention Of HIV Infection", *Biotech. Therap.* 2:31-48.

Katinger, H., (1994) "Human Monoclonal Antibodies For Passive Immunotherapy Of HIV-1" *Antibiot. Chemother.* 46:25-37.

Maddon, P.J. et al., (1986) "The T4 Gene Encodes The AIDS Virus Receptor And Is Expressed In The Immune System And The Brain", *Cell* 47:333-348.

Max, E., "Immunoglobulins: Molecular Genetics" Fundamental Imunology, 4th Edition. Lippincott-Raven Publishers, Philadelphia, 1999 pp. 11-182.

Queen, C. et al., (1989) "A Humanized Antibody That Binds To The Interleukin 2 Receptor", *Proc. Natl. Acad. Sci.* 86:10029-10033.

Sato, A.I. et al., (1992) "Anti-CD7 Reagents Inhibit HIV-1 Induced Syncytium Formation," International Conference On AIDS. 81. PA5 Poa 2017.

Sato, A.I. et al., (1994) "Identification Of CD7 Glycoprotein As An Accessory Molecule In HIV-1 Mediated Syncytium Formation And Cell Free Infection", *J. Immunol.* 152:5142-5152.

Sato, A.I. et al., (1995) "A Simple And Rapid Method For Preliminary Evaluation Of In Vivo Efficacy Of Anti-HIV Compounds In Mice", *Antivir. Res.* 27:151-163.

Schanberg, L.W. et al., (1995) "Characterization Of Human CD7 Transgenic Mice", *J. Of Immunol.* 155:2407-2418.

Sommerfelt, M.A. et al., (1995) "Intercellular Adhesion Molecule 3, A Candidate Human Immunodeficiency Virus Type 1 Co-Receptor On Lymphoid And Monocytoid Cells", *J. Gen. Virol.* 76:1345-1352.

Tulip, W.R. et al., (1992) "Crystal Structures Of Two Mutant Neraminidase-Antibody Complexes With Amino Acid Substitutions In The Interface", *J. Mol. Biol.* 227:149-159.

Valentin, A. et al., (1990) "The Leukocyte Adhesion Glycoprotein CD18 Participates In HIV Induced Syncytia Formation In Monocytoid And T Cells", *J. Immunol.* 144:934-937.

Wang, Z.Q. et al., (1994) "Deletion Of T Lymphocytes In Human CD4 Transgenic Mice Induced By HIV-gp120 And gp120-Specific Antibodies From AIDS Patients", *Eur. J. Immunol.* 24:1553-1557.
U. S. Appl. No. 09/663,219, filed Sep. 15, 2000, Olson et al.
U.S. Appl. No. 10/081,128, filed Feb. 22, 2002, Olson et al.
U.S. Appl. No. 09/212,793, filed Dec. 16, 1998, Olson et al.
U.S. Appl. No. 08/168,311, filed Dec. 17, 1993, Allaway et al.
U.S. Appl. No. 08/475,515, filed Jun. 7, 1995, Allaway et al.
U.S. Appl. No. 08/587,458, filed Jan. 17, 1996, Litwin et al.
U.S. Appl. No. 08/627,684, filed Apr. 2, 1996, Allaway et al.
U.S. Appl. No. 08/663,616, filed Jun. 14, 1996, Allaway et al.
U.S. Appl. No. 08/663,171, filed Jun. 14, 1996, Allaway et al.
U.S. Appl. No. 08/665,090, filed Jun. 14, 1996, Allaway et al.
U.S. Appl. No. 08/673,682, filed Jun. 25, 1996, Allaway et al.
U.S. Appl. No. 08/874,570, filed Jun. 13, 1997, Allaway et al.
U.S. Appl. No. 08/874,618, filed Jun. 13, 1997, Allaway et al.
U.S. Appl. No. 09/118,415, filed Jul. 17, 1998, Litwin et al.
U.S. Appl. No. 09/724,105, filed Nov. 28, 2000, Allaway et al.
U.S. Appl. No. 60/358,886, filed Feb. 22, 2002, Olson et al.
U.S. Appl. No. 60/014,532, filed Apr. 2, 1996, Allaway et al.
U.S. Appl. No. 60/017,157, filed May 20, 1996, Littman et al.
U.S. Appl. No. 60/266,738, filed Feb. 6, 2001, Olson et al.
U.S. Appl. No. 60/282,380, filed Apr. 6, 2001, Olson et al.
U.S. Appl. No. 60/019,715, filed Jun. 14, 1996, Olson et al.
U.S. Appl. No. 60/019,941, filed Jun. 14, 1996, Allaway et al.
U.S. Appl. No. 60/112,532, filed Dec. 16, 1998, Olson et al.
U.S. Appl. No. 60/185,667, filed Feb. 29, 2000, Dragic et al.
U.S. Appl. No. 60/205,839, filed May 19, 2000, Dragic et al.
U.S. Appl. No. 60/267,231, filed Feb. 7, 2001, Dragic et al.
U.S. Appl. No. 60/272,203, filed Feb 28, 2001, Dragic et al.
U.S. Appl. No. 60/018,508, filed May 28, 1996, Combadiere et al.
PCT International Preliminary Examination Report issued Oct. 18, 1996 for International Application Publication No. WO 95/16789.
PCT International Preliminary Examination Report issued Sep. 5, 1997 for International Application Publication No. WO 96/41020.
PCT International Preliminary Examination Report issued Jan. 27, 2000 for International Application Publication No. WO 98/56421.
PCT International Preliminary Examination Report issued Jul. 10, 1998 dor International Application Publication No. WO 97/37005.
PCT International Preliminary Examination Report issued Oct. 16, 1999 for International Application Publication No. WO 97/47319.
PCT International Preliminary Examination Report issued Sep. 28, 2005 for International Application Publication No. WO 03/072766.
PCT International Preliminary Examination Report issued Apr. 5, 2006 for International Applicatio Publication No. WO 03/072766.
PCT International Preliminary Examination Report issued Feb. 15, 2001 for International Application Publication No. WO 00/35409.
PCT International Preliminary Examination Report issued Dec. 24, 2003 for International Application Publication No. WO 02/083172.
PCT International Search Report issued Mar. 13, 1995 for International Application Publication No. WO 95/16789.
PCT International Search Report issued Oct. 10, 1996 for International Application Publication No. WO 96/41020.
PCT International Search Report issued Jul. 5, 1997 for International Application Publication No. WO 98/56421.
PCT International Search Report issued Sep. 12, 1998 for International Application Publication No. WO 98/56421.
PCT Intertnational Search Report issued Sep. 3, 1997 for International Application Publication No. WO 97/47319.
PCT International Search Report issued Sep. 3, 1997 for International Application Publication No. WO 97/47318.
PCT International Search Report issued Jun. 7, 2000 for International Application Publication No. WO 00/35409.
PCT International Search Report issued Aug. 13, 2003 for International Application Publication No. WO 03/072766.
PCT International Search Report issued Apr. 23, 2002 for International Application Publication No. WO 02/22077.
PCT International Search Report issued Jul. 31, 2003 for International Application Publication No. WO 02/083172.
PCT Written Opinion issued May 25, 2005 in connection with International Application Publication No. WO 03/072766.
European Supplementary Search Report issued Apr. 21, 2006 for European Application No. 03713632.2.
European Supplementary Partial Search Report issued Sep. 27, 2004 for European Application No. 99966466.
European Supplementary Search Report issued Sep. 5, 2002 for European Patent Application No. 95905987.4.
European Supplementary Search Report issued Feb. 24, 2000 for European Patent Application No. 96921473.3
European Supplementary Search Report issued Mar. 6, 2002 for European Patent Application No. 97917856.3.
European Supplementary Partial Search Report issued Feb. 19, 2003 for European Patent Application No. 98931261.6.
European Supplementary Partial Search Report issued Aug. 26, 2004 for European Patent Application No. 97930120.7.
European Supplementary Partial Search Report issued Nov. 8, 2004 for European Patent Application No. 97930120.7.
Apr. 21, 2006 Supplementary European search report under Article 157(2)(a) in connection with European Application No. 03 713 632.2.
Feb. 9, 2004 Office action in connection with U.S. Appl. No 10/116,797.
Alkhatib, G., et al. (1996). CC CKR5: A Rantes, MIP-1a, MIP-1β Receptor As A Fusion Cofactor For Macrophage-Tropic HIV-1. Science, 272:1955-1958.
Alkhatib, G., et al. (1997). HIV Co-Receptor Activity Of CCR5 And Its Inhibition By Chemokines: Independence From G Protein Singaling . . . Virology, 234:340-348.
Allan, J. (1997) "Human Immunodeficiency . . . ", in AIDS: Biology, Diagnosis, . . . , 4th edition, De Vita, Jr., et al., eds., Lippincott-Raven Publishers, Philadelphia. pp. 15-27.
Allaway, G.P., et al. (1993). Synergistic Inhibition Of HIV-1 Envelope-Medicated Cell Fusion By CD4-Based Molecules in Combination . . . AIDS Res. Hum. Retroviruses, 9:581-587.
Allaway, G.P., (1995). Expression And Characterization Of CD4-IgG2, A Novel Heterotetramer That Neutralizes Primary HIV Type 1 Isolates. AIDS Res. Hum. Retrovirus, 11:533-539.
Amara, A., et al. (1997). HIV Coreceptor Downregulation As Antiviral Principle: SDF-La-Dependent Internalization Of The . . . J. Exp. Med., 186:139-146.
Arenzana-Selsdedos, F., et al. (1996). HIV Blocked By Chemokine Antagonist. Nature, 383:400.
Arthos, J., et al. (1989). Identification Of The Residues In Human CD4 Critical For The Binding Of HIV. Cell, 57:469-481.
Baba, et al. (1998). Mechanism Of Inhibitory Effect Of Dectran Sulfate And Heparin On Replication Of Human Immunodeficiency Virus In . . . Proc. Natl. Acad. Sci., 85:6132-6135.
Back, D.J. (1999). Pharmacological Issues Relating To Viral Resistance. Infection, 27(Suppl.2):S42-S44.
Balzarini, et al. (1995). Suppression Of The Breakthrough Of HIV-1 In Cell Culture By Thiocarboxanilide Derivatives When Used . . . Proc. Natl. Acad. Sci., 92:5470-5474.
Baulerle and Huttner (1987). Tyrosine Sulfation Is A Trans-Golgi-Specific Protein Modification. Cell. Biol., 105:2655-2663.
Benet, et al. (1990). "Pharmacokinetics: . . . ", in Goodman And Gilman's The Pharmacological Basis of Therapeutics, Gilman, et al., eds., Pergamon Press, New york. pp. 3-32.
Berger, et al. (1996). Abstract No. 002, 8 at Keystone Symposium.
Berger E.A. (1997). HIV Entry And Tropism: The Chemokine Receptor Connection. AIDS, 11(Suppl.A):S3-S16.
Berger, et al. (1999). Chemokine Receptors As HIV-1 Coreceptors: Roles In Viral Entry, Tropism And Disease. Ann. Rev. Immunol., 17:657-700.
Bieniasz, P.D., et al. (1997), HIV-1 Induced Cell Fusion Is Mediated By Multiple Regions Within Both the Viral Envelope And The CCR5 Co-Receptor. EMBO, 16:2599-2609.
Blanpain, C., et al. (1999). Multiple Charged And Aromatic Residues In CCR5 Amino-Terminal Domain Are Involved In High Affinity Binding . . . J. Biol. Chem., 274:34719-34727.
Bleul, C.C., et al. (1991). the Lymphocyte Chemoattractant SDF-1 Is A Ligand For LESTR/Fusion And Blocks HIV-1 Entry. Nature, 382:829-832.
Brelot, A., et al. (1997). Role Of The First And Third Extracellular Domains Of CXCR4 In Human Immunodeficiency Virus Coreceptor Activity. J. Virol., 71:4744-4751.

European Supplementary Search Report issued Apr. 27, 2006 for European Patent Application No. 01970984.9.

European Patent Office Communication issued Nov. 11, 2004 in connection with European Patent Application No. 97930120.7.

Feb. 27, 2004 Third Party Observations in connection with European Application No. 97904948.3.

Alkhatib, et al. (1996). Abstract At 3rd Conference On Retroviruses. Genbank Sequence Report, Accession Entry X91492 for H. sapiens Chem13, submitted Sep. 14, 1995.

Janeway and Travers (1994). Immunobiology, Current Biology Ltd., San Francisco. pp. 10:27-10:42.

Stryer (1988). Biochemistry, 3rd edition. pp. 984-988.

Dec. 17, 2003 Third Party Observations in connection with European Application No. 97904948.3.

Sep. 7, 2005 Office Action in connection with U.S. Appl. No. 09/888,938.

Apr. 21, 2006 Supplementary European search report under Article 157(2)(a) in connection with European Application No. 03 713 632.2.

Broder, et al. (1996). HIV And The 7-Transmembrane Domain Receptors. Pathobiology, 64(4):171-179.

Burkly, L., et al. (1995). Synergistic Inhibition Of Human Immunodeficiency Virus Type 1 Envelope Glycoprotein-Mediated Cell . . . J. Virol., 69:4267.4273.

Burton, D.R., et al. (1994). Efficient Neutralization Of Primary Isolates Of HIV-1 By A Recombinant Human Monoclonal Antibody. Science, 266:1024-1027.

Camerini, D., et al. (1990). A CD4 Domain Important For HIV-Mediated Syncytium Formation Lies Outside The Virus Binding Site. Cell, 60(5):747-754.

Cammack, N. (1999). Human Immunodeficiency Virus Type 1 Entry And Chemokine Receptors: A New Therapeutic Target. Antiviral Chemistry And Chemotherapy, 10:53-62.

Capon, D.J., et al. (1989). Designing CD4 Immunoadhesions For AIDS Therapy. Nature, 337:525-531.

Chams, et al. (1992). Simple Assay To Screen For Inhibitors Of Interaction Between The Human Immunodeficiency Virus Envelope . . . Antimicrob Agents Chemother., 36(2):262-272.

Chan, D.C., et al. (1998). Evidence That A Prominent Cavity In The Coiled Coil Of HIV Type 1 Gp41 Is An Attractive Drug Target. Proc. Natl. Acad. Sci., 95:15613-15617.

Chan, D.C., et al. (1998). HIV Entry And Its Inhibition. Cell, 93:681-684.

Charo, et al. (1994). Molecular Cloning And Functional Expression Of Two Monocyte Chemoattractant Protein 1 Receptors Reveals . . . Proc. Natl. Acad. Sci., 91:2752-2756.

Chen, et al. (1997). Genetically Divergent Strains Of Simian Immunodeficiency Virus Use CCR5 As A Coreceptor For Entry. J. Of Virol., 71(4):2705-2714.

Choe, H., et al. (1996). The Beta-Chemokine Receptors CCR3 And CCR5 Facilitate Infection By Primary HIV-1 Isolates. Cell, 85:1135-1148.

Clapham, P.R., et al. (1989). Soluble CD4 Blocks the Infectivity Of Diverse Strains Of HIV And SIV For T Cells And Monocytes But Not For Brain And . . . Nature, 337:368-370.

Co, et al. (1991). Humanized Antibodies For Antiviral Therapy. Proc. Natl. Acad. Sci., 88:2869-2873.

Cocchi, F. (1995). Identification Of Rantes, MIP-1 alpha And MIP-1 beta As The Major HIV-Suppressive Factors Produced By CD8+ T-Cells. Science, 270:1811-1815.

Combadiere, et al. (1995). Cloning And Functional Expression Of A . . . J. Biol. Chem., 270, 16491-16494 (NOTE- Erratum In: J Biol Chem 1995 Dec. 15;270(50):30235)).

Combadiere, et al. (1996). Cloning And Fuctional Expression Of CC CKR5, A Human Monocyte CC Chemokine Receptor Selective For MIP-1a, . . . J. Leukos. Biol., 60:147-152.

Connor, R.I., et al. (1997). Change In Co-Receptor Use Correlates With Disease Progression In HIV-1 Infected Individuals. J. Exp. Med., 185:621-628.

Cormier, E.G., et al. (2000). Specific Interaction Of CCR5 Amino-Terminal Domain Peptides Containing Sulfotyrosines With HIV-1 . . . Proc. Natl. Acad. Sci., 97:5762-5767.

Crowe, S.M., et al. (1992). Human Immunodeficiency Virus-Infected Monocyte-Derived Macrophages Express Surface Gp120 And . . . Clin. Immunol Immunopathol., 65(2):143-151.

Crump, M.P., et al. (1997). Solution Structure And Basis For Functional Activity Of Stromal-Cell Derived Factor-1: Disassociation . . . EMBO, 16:6996-7007.

Cruse, et al. (1995). Illustrated Dictionary Of Immunology, CRC Press, Inc, Boca Raton, FL., 143:QR180.4.C78.

Cushman, M., et al. (1991). Preparation And Anti-HIV Activities Of Aurintricarboxylic Acid Fractions And Analogues: Direct Correlation . . . J. Med. Chem., 34:329-337.

Daar,.E.S. (1990). High Concentrations Of Recombinant Soluble CD4 Are Required To Neutralize Primary Human Immunodeficiency Virus . . . Proc. Natl. Acad. Sci., 87:6574-6578.

Dalgleish, A. G., et al. (1984). The CD4 (T4) Antigen Is An Essential Component Of The Receptor For The AIDS Retrovirus. Nature, 312:763-766.

De Rossi, A., et al. (1995). Synthetic Peptides From The Principle Neutralizating Domain Of Human Immunodeficiency Virus Type 1 (HIV-1) . . . Virology, 184:187-196.

Dean, M., et al. (1996). Genetic Restriction Of HIV-1 Infection And Progression To AIDS By A Deletion Allele Of The CKR5 Structural Gene. Science, 273:1856-1862.

De Clerq, et al. (1992). Potent And Selective Inhibition Of Human Immunodeficiency Virus (HIV)-1 and HIV-2 Replication By A Class Of . . . Proc. Natl. Acad. Sci., 89:5286-5290.

De Clerq, et al. (1994). Highly Potent And Selective Inhibition Of Human Immunodeficiency Virus By The Bicyclam . . . Antimicrobial Agents and Chemotherapy, 38:668-674.

De Clerq, et al. (1995). Antiviral Therapy For Human Immunodeficiency Virus Infections. J. Clin. Microbiol. Rev., 8(2):200-239.

Deen, K.C., et al. (1988). A Soluble Form Of CD4(T4) Protein Inhibits AIDS Virus Infection. Nature, 331:82-84.

Deng, H., et al. (1996). Identification Of A Major Co-Receptor For Primary Isolates Of HIV-1. Nature, 381:661-666.

Deng, X., et al. (1999). A Synthetic Peptide Derived From Human Immunodeficiency Virus Type 1 Gp120 Down-Regulates The Expression . . . Blood, 94(4):1165-1173.

Dettin, et al. (2003). CCR5 N-Terminus Peptides Enhance X4 HIV-1 Infection By CXCR4 Up-Regulation. Biochem. Biophys. Res. Commun., 307(3):640-646.

Dikic (1996). Regulation of HIV-1 Infection by Chemokine Receptors. Acta. Med. Croatica, 50:163-168.

Dimitrov, et al. (1991). Initial Stages of HIV-1 Envelope Glycoprotein-Mediated Cell Fusion Monitored By A New Assay Based On . . . AIDS Res. Hum. Retroviruses, 7(10):799-805.

Ditzel, et al. (1998). The CCR5 Receptor Acts As An Alloantigen In CCR5Δ32 Homozygous Individuals: Identification Of Chemokine And . . . Proc. Natl. Acad. Sci., 95(9):5241-5245.

Donzella, G.A., et al. (1998). AMD3100, A Small Molecule Inhibitor Of HIV-1 Entry Via The CXCR4 Co-Receptor. Nat. Med., 4:72-77.

Doranz, B.J., et al. (1996). A Dual-Tropic Primary HIV-1 Isolate That Uses Fusin And Beta-Chemokine Receptors CKR-5, CKR-3 And CKR-2b . . . Cell, 85:1149-1158.

Doranz, B.J., et al. (1997). Two Distinct CCR5 Domains Can Mediate Co-Receptor Usage By Humas Immunodeficiency Virus Type 1. J. Virol., 71:6305-6314.

Doranz, B.J., et al. (1997). A Small Molecule Inhibitor Directed Against The Chemokine Receptor CXCR4 Prevents Its Use As An HIV-1 Co-Receptor. J. Ex. Med., 186:1395-1400.

Dragic, T.V., et al. (1993). Different Requirements For Membrane Fusion Mediated By The Envelopes Of Human Immunodeficiency Virus Types 1 And 2. J. Virol., 67(4):2355-2359.

Dragic, T.V., et al. (1996). HIV-1 Entry Into CD4+Cells Is Mediated By The Chemokine Receptor CC-CKR-5. Nature, 381:667-673.

Dragic, T.V., et al. (1998). Amino-Terminal Substitutions In The CCR5 Coreceptor Impair Gp120 Binding And Human Immunodeficiency Virus Type 1 Entry. J. Virol., 72(1):279-285.

Dragic, et al. (2000). A Binding Pocket For A Small Molecule Inhibitor Of HIV-1 Entry Within The Transmembrane Helices Of CCR5. Proc. Natl. Acad. Sci., 97(10):5639-5644.

Ebadi, M. (1998). the Pharmacokinetic Basis Of therapeutics. CRC Desk Reference Of Clinical Pharmacology, pp. 1-7.

Eckert, D.M., et al. (1999). Inhibiting HIV-1 Entry: Discovery Of D-Peptide Inhibitors That Target The gp41 Colied-Cil Pocket. Cell, 99:103-115.

Eugen-Olsen, J., et al. (1997). Heterozygosity For A Deletion In The CKR-5 Gene Leads To Prolonged AIDS-Free Survival And Slower CD4 . . . AIDS, 11:305-310.

Fahey, J.L., et al. (1992). Status Of Immune-Based Therapies In HIV Infection And AIDS. Clin. Exp. Immunol., 88:1-5.

Farzan, M., et al. (1998). A Tyrosine-Rich Region In The N-Terminus Of CCR5 is Important For Human Immunodeficiency Virus Type 1 Entry . . . J. Virol., 72:1160-1164.

Farzan, M., et al. (1999). Tyrosine Sulfation Of The Amino-Terminus Of CCR5 Facilitates HIV-1 Entry. Cell, 96:667-676.

Farzan, M., et al. (2000). A tyrosine-sulfated peptide based on the N terminus of CCR5 interacts with a CD4-enhanced epitope of the . . . J. Biol. Chem., 275:33416-33521.

Feng, et al. (1996). Abstract No. 116,21 at Keystone Symposium.

Feng, Y., et al. (1996). HIV-1 Entry Cofactor: Functional cDNA Cloning Of A Seven-Transmembrane, g Protein-Coupled Receptor. Science, 272:872-877.

Ferrer, M., et al. (1999). Selection Of gp-41 Mediated HIV-1 Cell Entry Inhibitors From Biased Combinatorial Libraries Of Non-Natural . . . Nature. Struct. Biol., 6:953-959.

Flexner, C. and Hendrix, C. (1997). "Pharmacology Of . . . ", in AIDS: Biology, Diagnosis, . . . , 4th Edition, De Vita V., et al. eds., Lippincott-Raven Publishers. pp. 479-493.

Fouchier, et al. (1994). HIV-1 Macrophage Tropism Is Determined At Multiple Levels Of The Viral Replication Cycle. J. Clin. Invest., 94:1806-1814.

Fouts, T.R., et al. (1997). Neutralization Of The Human Immunodeficiency Virus Type 1 Primary Isolate JR-FL By Human . . . J. Virol., 71:2779-2785.

Fox, J.L. (1994). No Winners Against Aids. Bio/Technology, 12:128.

Freed, E.O., et al. (1991), Identification Of Conserved Residues In The Human Immunodeficiency Virus Type 1 Principle . . . AIDS Res. Hum. Retroviruses, 7(10):807-811.

Fradd, F. and Mary, M.E. (1989). AIDS Vaccines: An Investor's Guide, Shearman Lehaman Hutton. p. 10:(Fig. 2).

Frazer, J.K. and Capra, J.D. (1999). "Immunoglobulins . . . ", in Fundamental Immunology, 4th Edition, W.E. Paul, ed., Lippincott-Raven Publishers, Philadelphia. pp. 111-182.

Furuta, R.A., et al. (1998). Capture Of An Early Fusion-Active Conformation Of HIV-1 gp41. Nature Struct. Biol., 5(4):276-279.

Gait, M.J and Karn, J. (1995). Progress In anti-HIV Structure Based Drug Design. Tibtech, 13:430-438.

Gauduin, M.C., et al. (1996). Effective Ex Vivo Neutralization Of Plasma HIV-1 By Recombinant Immunoglobulin Molecules. J. Virol., 70:2586-2592.

Gauduin, M.C., et al. (1997). Passive Immunization With A Human Monoclonal Antibody Protects hu-PBL-SCID Mice Against Challenge . . . Nature Medicine, 3:1389-1393.

Ghorpade A., et al. (1998). Role Of The Beta-Chemokine Receptors CCR3 And CCR5 In Human Immunodeficiency Virus Type 1 Infection Of . . . J. Virol, 72:3351-3361.

Gong, J.H., et al. (1995). Antagonists Of Monocyte Chemoattractant Protein 1 Identified By Modification Of Functionally Critical . . . J. Exp. Med., 181:631-640.

Gong, J.H., et al. (1996). Rantes And MCP-3 Antagonists Bind Multiple Chemokine Receptors. J. Biol. Chem., 371:10521-10527.

Graham, et al. (1995). Candidate Aids Vaccines. New Engl. J. Med., 333:1331-1339.

Grene, et al. (2001). Anti-CCR5 Antibodies In Sera Of HIV-Positive Individuals. Human Immunol., 62(2):143-145.

Harouse, J.M., et al. (1991). Inhibition Of Entry Of HIV-1 In Neural Cell Lines By Antibodies Against Galactosyl Ceramide. Science, 253(5017):320-323.

Haynes, B.F. (1996). Updates On The Issues Of HIV Vaccine Development. Ann. Med., 28:39-41.

He, Jianglin, et al. (1997). CCR3 And CCR5 Are Co-Receptors For HIV-1 Infection Of Microglia. Nature, 385:645-649.

Health, et al. (1997). Chemokine Receptor Usage By Human Eosinophils. The Importance Of CCR3 Demonstrated Using An . . . J. Clin. Invest., 99:178-184.

Heidenreich, et al. (1995). Application Of Antisense Technology To Therapeutics. Mol. Med. Today, 1:128-133.

Hill, C.M., et al. (1998). The Amino Terminus Of Human CCR5 Id Required For Its Function As A Receptor To Diverse Human And Simian . . . Virology; 248:357-371.

Hirata, Y. (1989). Characterization Of IL-6 Receptor Expression By Monoclonal And Polyclonal Antibodies. J. Immun., 2900-2906.

Hirsch, et al. (1997). "Antiretroviral . . . ", in AIDS: Biology, Diagnosis, . . . , 4th Edition, De Vita, Jr., et al. eds., Lippincott-Raven Publishers, Philadelphia. pp. 495-508.

Howard, O.M.Z., et al. (1998). Small Molecule Inhibitor Of HIV-1 Cell Fusion Blocks Chemokine Receptor-Mediated Fusion. J. Leuk. Biol., 64:6-13.

Hwang, S.S., et al. (1991). Identification Of The Envelope V3 Loop As The Primary Determinant Of Cell Tropism In HIV-1. Science, 253:71-74.

Jacobson, J., et al. (1999). Results Of A Phase I Trial Of . . . Abstracts Of The 39th Interscience Conference On Antimicrobial Agents And Chemotherapy 14.

Ji, H., et al. (1999). Inhibition Of Human Immunodeficiency Virus Type 1 Infectivity By The gp41 Core: Role Of A Conserved Hydrophobic . . . J. Virol., 73:8578-8586.

Jiang, S., et al. (1993). HIV-1 Inhibition By A Peptide. Nature, 365:113.

Jones, S.A., et al. (1997). Chemokine Antagonist That Discriminate Between Interleukin-8 Receptors. J. Biol. Chem., 272:16166-16199.

Keller, P.M., et al. (1977). A Fluorescence Enhancement Assay Of Cell Fusion. J. Cell Sci., 28:167-177.

Kilby, J.M., et al. (1998). Potent Suppression Of HIV-1 Replication In Humans By T-20, A Peptide Inhibitor Of gp41-Mediated Virus Entry. Nature Med., 4:1302-1307.

Klotman, et al. (1995). Trasgenic Models Of HIV-1. AIDS, 9(4):313-324.

Konigs, C., et al. (2000). Monoclonal Antibody Screening Of Phage-Displayed Random Peptide Library Reveals Mimotopes Of Chemokine . . . Eur. J. Immnol., 30(4):1162-1171.

Konishi, K., et al. (2000). Synthesis Of Peptides Mimicking Chemokine Receptor CCR5 And Their Inhibitory Effects Against HIV-1 . . . Chem. Pharm. Bull., Tokyo, 48(2):308-309.

Koup, R.A., et al. (1996). Defining Antibody Protection Against HIV-1 Transmission In Hu-PBL-SCID Mice. Immunology, 8:263-268.

Kwong, P.D., et al. (1998). Structure Of An HIV gp120 Envelope Glycoprotein In Complex With The CD4 Receptor And Neutralizing Human Antibody. Nature, 393:648-659.

Laal, S., et al. (1994). Synergistic Neutralization Of Human Immunodeficiency Virus Type 1 By Combinations Of Human Monoclonal Antibodies. J. Virol., 68:4001-4008.

LaCasse, R.A., et al. (1999). Fusion-Competent Vaccines: Broad Neutralization Of Primary Isolates Of HIV. Science, 283:357-362.

Lee, B., et al. (1999). Epitope Mapping Of CCR5 Reveals Multiple Conformational States And Distinct But Overlapping Structures . . . J. Biol. Chem., 9617-9626.

Lehner, et al. (2001). Immunogenicity Of The Extracellular Domains Of C-C Chemokine Receptor 5 And The In Vitro Effects On Simian . . . Journal Of Immunology, 166(12):7446-7455.

Levy, J.A., (1996). Controlling HIV Pathogenesis: The Role Of The Non-Cytotoxic Anti-HIV Response Of CD8+ Cells. Immunology Today, 17:217-224.

Li, A., et al. (1997). Synergistic Neutralization Of Chimeric SIV/HIV Type 1 Virus With Combinations Of Human Anti-HIV Type 1 . . . AIDS Res. Hum. Retroviruses, 12:647-56.

Li, A.H., et al. (1998). Synergistic Neutralization Of Simian-Human Immunodeficiency Virus SHIV-vpu+ By Triple And Quadruple Combination . . . J. Virol., 72:3235-3240.

Litwin, V. M., et al. (1996). Human Immunodeficiency Virus Type 1 Membrane Fusion Mediated By A Laboratory-Adapted Strain And A . . . J. Virol., 70(9):6437-6441.

Loetscher, M., et al. (1994). Cloning Of A Human Seven-Transmembrane Domain Receptor, Lester, That Is Highly Expressed In Leukocytes. J. Biol. Chem., 269:232-237.

Mack, M.m et al. (1998). Aminooxypentane-Rantes Induces CCR5 Internalization But Inhibits Recycycling: A Novel Inhibitory . . . J. Ex. Med., 187:1215-1224.

Mackay, C.R. (1996). Chemokine Receptors And T Cell Chemotaxis. J. Exp. Med., 84:799-802.

Markosyan, R.M., et al. (2002). The Mechanism Of Inhibition Of HIV-1 Env-Mediated Cell-Cell Fusion By Recombinant Cores Of gp41 Ectodomain. Virology, 302:174-184.

Mateu, M.G., et al. (1992). Non-Additive Effects Of Multiple Amino Acid Substitutions On Antigen-Antibody Recognition. European J. Immunol., 22(6):1385-1389.

McKnight, A.D., et al. (1997). Inhibition Of Human Immunodeficiency Virus Fusion By A Monoclonal Antibody To A Coreceptor (CXCR4) Is . . . J. Virol., 71:1692-1696.

Mellors, J.W. (1996). Closing In On Human Immunodeficiency Virus-1. Nature Medicine, 2(3):274-275.

Mitsuya, H., et al. (1985). "Protection . . . " in Retroviruses in Human Lymphoma Leukemia, Miwa, et al. eds., Japan Sci. Soc. Press, Tokyo/VNU Science Press, Utrecht. pp. 277-288.

Mittler, R.S., et al. (1989). Synergism Between Hiv gp120 And gp120-Specific Antibody In Blocking Human T. Cell Activation. Science, 245:1380-1382.

Mohan, P., et al. (1992). Sulfonic Acid Polymers As A New Class Of Human Immunodeficiency Virus Inhibitors. Antiviral Res., 18:139-150.

Moser, B., et al. (1993). Interleukin-8 Antagonists Generated By N-Terminal Modification. J. Biol. Chem., 268:7125-7128.

Mosier, D.E. (1990). Immunodeficient Mice Xenografted With Human Lymphoid Cells: New Models For in-Vivo Studies Of Human . . . J. Clin. Immuno., 10(4):185-191.

Nagasawa, et al. (1994). Molecular Cloning And Structure Of A Pre-B-Cell Growth-Stimulating Factor. Proc. Natl. Acad. Sci., 91:2305-2309.

Nagashima, K.A., et al. (2001). Human Immunodeficiency Virus Type 1 Entry Inhibitors PRO 542 And T-20 Are Potently Synergistic In . . . J. Infect. Dis., 183:1121-1125.

Nakano, T., et al. (1995). Vascular smooth muscle cell-derived, Gla-containing growth-potentiating factor for Ca2+ mobilizing growth . . . J. Biol. Chem., 270(11):5702-5705.

Neote, et al. (1993). Molecular cloning, functional expression, and signaling characteristics of a C-C chemokine receptor. Cell, 72:415-425.

O'Brien, et al. (1990). HIV-1 Tropism for Mononuclear Phagocytes can be Determined by Regions of gp120 Outside of the CD4-binding domain, Nature, 348:69-73.

Oberg, B and Vrang, L. (1990). Screening for new agents. Eur. J. Clin. Microbiol. Infect. Dis., 9(7):466-471.

Oberlin, E., et al. (1996). The CXC Chemokine SDF-1 is the Ligand for LESTR/fusion and prevents infection by T-cell-line-adapted HIV-1. Nature, 382:833-835.

Oellerich, M., (1984). Enzyme-Immunoassay: A Review. J. Clin. Chem. Clin. Biochem., 22(12):895-904.

Olson, et al., (1999). Differential Inhibition of Human Immunodeficiency Virus Type 1 Fusion, gp120 Binding and CC-chemokine Activity of Monoclonal . . . J. Virol. 73:4145-4155.

Opperman, (2004). Chemokine Receptor CCR5: Insights Into Structure, Function, And Regulation. Cell. Signal., 16:1201-1210.

Parren, et al. (2001). Antibody Protects Macaques Against Vaginal Challenge With A Pathogenic R5 Simian/Human Immunodeficiency Virus . . . J. Virol., 75:8340-8347.

Partidos, C., et al. (1992). The Effect Of Orientation Of Epitopes On The Immunogenicty Of Chimeric Synthetic Peptides Representing . . . Molecular Immunology, 29(5):651-658.

Perden, et al. (1991). Changes In Growth Properties On Passage In Tissue Culture Of Viruses Derived From Infectious Molecular Clones . . . Virol., 185:661-672.

Poignard, P., et al. (1999). Neutralizing Antibodies Have Limited Effects On The Control Of Established HIV-1 Infection in-Vivo. Immunity, 10:431-438.

Posner, M.R., et al. (1993). Neutralization Of HIV-1 By F105, A Human Monoclonal Antibody To The CD4 Binding Site Of gp120. J. Acq. Immune Defic. Synd., 6:4-14.

Power, et al. (1995). Molecular Cloning And Functional Expression Of A Novel CC Chemokine Receptor cDNA From A Himan Basophilic Cell Line. J. Biol. Chem., 270:1811-1815.

Proudfoot, et al. (1996). Extension Of Recombinant Human RANTES By The Retention Of The Initiating Methionine Produces A Potent Antagonist. J. Biol. Chem., 271:2599-2603.

Proudfoot, et al. (1999). Chemokine Receptors: Future Therapeutic Targets For HIV. Biochem. Pharmacol., 57:451-463.

Proudfoot, et al. (2000). The Strategy Of Blocking The Chemokine System To Combat Disease. Immunol. Rev., 177:246-256.

Rabut, G.E., et al. (1991). Alanine Substitutions Of Polar And Nonpolar Residues In The Amino-Terminal Domain Of CCR5 Differently . . . J. Virol., 72:3464-3468.

Raport, C.J., et al. (1996). Molecular Cloning And Functional Characterization Of A Novel Human CC-Chemokine Receptor (CCR5) For . . . J. Biol. Chem., 271:1761-1766.

Raport, C. J., et al. (1996). New Members Of The Chemokine Receptor Gene Family. Journal of Leukocyte Biology, 59:18-23.

Raport, C.J., et al. (1996). AAC50598 submitted to NCBI on Apr. 12, 1996 (CC Chemokine Receptor 5 sequence).

Richman, D.D. (1996). Antiretroviral Drug-Resistance: Mechanism, Pathogenesis, Clinical Significance. Antivir. Chemother., 4:383-395.

Rodriguez, G., et al. (1995). Mediation Of Human Immunodeficiency Virus Type 1 Binding By Interaction Of Cel Surface Heparin Sulfate . . . J. Virol., 69:2233-2239.

Rucker, et al. (1996). Regions In Beta-Chemokine Receptors CCR5 And CCR2b That Determine HIV-1 Cofactor Specificity. Cell, 87:437-446.

Ruffing, et al. (1998). CCR5 Has An Expanded Ligand-Binding Repertoire And Is The Primary Receptor Used By MCP-2 On Activated T-Calls. Cell. Immunol., 160:160-168.

Rudikoff, et al. (1982). Single Amino Acid Substitution Altering Antigen-Binding Specificity. Proc. Natl. Acad. Sci., 79:1979-1983.

Rusche, et al. (1988). Antibodies That Inhibit Fusion Of Human Immunodeficiency Virus-Infected Cells Bind A 24-Amino Acid Sequence . . . Proc. Natl. Acad. Sci., 85:3198-3202.

Sagg, M. (1997). "Clinical Spectrum Of . . . ", in AIDS: Biology, Diagnosis, . . . , De Vita et al., eds., Lippincott-Raven Publishers, Philadelphia. pp. 202-213.

Samson, M., et al. (1996). Molecular Cloning And Functional Expression Of A New Human CC-Chemokine Receptor Gene. Biochem., 35:3362-3367.

Sandberg, J. (1995). Developmental Pharmacology And Toxicology Of Anti-HIV Therapeutic Agents: Dideoxynucleosides. FASEB J., 9:1157-1163.

Sandstorm, E.G. and Kaplan, J.C. (1987). Antiviral Therapy In AIDS: Clinical Pharmacological Properties And Therapeutic Experience To Date. Drugs, 34:372-390.

Scarlatti, et al. (1997). In Vivo Evolution Of HIV-1 Co-Receptor Usage And Sensitivity To Chemokine-Mediated Suppression. Nature Medicine, 3(11):A2581259-1265.

Schmidtmayerova, H., et al. (1993). Characterization Of HIV1-PAR, A Macrophage-Tropic Strain: Cell Tropism, Virus/Cell Entry And . . . Research in Virology, 144(1):21-26.

Schols, D., et al. (1990). Dextran sulfate and other Olyanionic anti-HIV compounds specifically interact with the viral gp120 . . . Virology, 175:556-561.

Schols, D., et al. (1991). Selective Inhibitory Activity Of Polyhydroxycarboxylates Derived From Phenolic Compounds Against . . . J. Acq. immune Defic. Synd., 4:677-685.

Schols, D., et al. (1999). CD26-Processed RANTES(3-68), But Not Intact RANTES, Has Potent Anti-HIV-1 Activity. Antiviral Res., 30:175-187.

Simmons, G., et al. (1997). Potent Inhibition Of HIV-1 Infectivity In Macropages And Lymphocytes By A Novel CCR5 Antagonist. Science, 276:276-279.

Sinangil, et al. (1988). Quantitative Measurement Of Fusion Between Human Immunodeficiency Virus And Cultured Cells Using Membrane Fluorescence Dequenching. FEB 239(1):88-92.

Stein, et al. (1993). Immune-Based Therapeutics: Scientific Rationale And Promising Approaches To The Treatment Of The Human . . . Clin. Onfect. Dis., 17:749-771.

Steinberger, P., et al. (2000). Generation And Characterization Of A Recombinant Human CCR5-Specific Antibody. J. Biol. Chem., 275:36073-36078.

Stewart, G.J. (1997). Increased Frequency Of CCR-5Δ32 Heterozygotes Among Long-Term Non-Progressors With HIV-1 Infection. AIDS, 11:1833-1838.

Strizki, J.M., et al. (1997). A Monoclonal Antibody (12G5) Directed Against CXCR4 Inhibits Infection With The Dual-Tropic Human . . . J. Virol., 71:5678-5683.

Su, et al. (1996). Preparation Of Specific Polyclonal Antibodies To A C-C Chemokine Receptor, CCR1, And Determination Of CCR1 Expression . . . J. Leukos. Biol., 60:658-666.

Szabo, et al. (1992). Cd4 Changes Conformation Upon Ligand Binding. J. Immunol. 149(11):3596-3604.

Szabo, G. Jr., et al. (1993). Specific Disengagement Of Cell-Bound Anti-LAM-1 (Anti-Selectin) Antibodies By Aurintricarboxylic Acid. Molecular Immunology, 30(18):1689-1694.

Thali, M., et al. (1992). Cooperativity Of Neutralizing Antibodies Directed Against The VS And CD4 Binding Regions Of The Human . . . J. Acq. Immune. Defic. Synd., 5:591-599.

Tilley, S.A. (1992). Synergistic Neutralization Of HIV-1 By Human Monoclonal Antibodies Against The V3 Loop And The . . . AIDS Research And Human Retroviruses, 80(4):461-467.

Tilley, S.A., et al. (1991). Potent Neutralization Of HIV-1 By Human And Chimpanzee Monoclonal Antibodies Directed Against Three . . . Sixieme Colloque Des Cent Gardes., 211-216.

Travis, B.M., et al., (1992). Fuctional Roles Of the V3 Hypervariable Region Of HIV-1 gp160 And . . . Virol. 186:313-317.

Tremblay, et al. (2000). Strong In Vitro Synergy Observed Between . . . Feb. 7th, 2000 Conference on Retroviruses and Opportunistic Infections, abstract 500.

Tremblay, et al. (1999). Strong In Vitro Synergy Between The Fusion Inhibitor T-20 And the CXCR4 Blocker . . . Journal of Acquired Immune Deficiency Syndromes, 25(2):99-102.

Trkola, A., et al. (2001). Potent, Broad-Spectrum Inhibition Of Human Immunodeficiency Virus Type 1 By The CCR5 Monoclonal Antibody PRO 140. J. Virol., 75:579-588.

Trkola, A., et al. (1999). Cross-Clade Neutralization Of Primary Isolates Of Human Immunodeficiency Virus Type 1 By Human Monoclonal . . . J. Virol., 73(5):4145-4155.

Trkola, A., et al. (1996). CD-4 Dependent, Antibody Sensitive Interactions Between HIV-1 And Its Co-Receptor CCR-5. Nature, 384:184-187.

Trkola, A., et al. (1998). Neutralization Sensitivity Of Human Immunodeficiency Virus Type 1 Primary Isolates To Antibodies And . . . J. Virol., 72:1876-1885.

Valenzuela, A., et al. (1997). Neutralizing Antibodies Against The V3 Loop Of Human Immunodeficiency Virus Type 1 Block The . . . J. Virol., 71(11):8289-8298.

Vanini, S., et al. (1992). Discrete Regions Of HIV-1 Gp41 Defined By Syncytia-Inhibiting Affinity-Purified Human Antibodies. AIDS, 7:176-174.

Verrier, F.C., et al. (1997). Antibodies To Several Conformation-Dependent Epitopes Of gp120/gp41 Inhibit CCR-5-Dependent . . . Proc. Natl. Acad. Sci., 94:9326-9331.

Vijh-Warrier, S., Pinter, A., Honnen, W.J., and Tilley, S.A. (1996). Synergistic Neutralization Of Human Immunodeficiency Virus Type 1 By . . . J. Virol., 70:4466-4473.

Vila-Coro, et al. (2000). HIV-1 Infection Through The CCR5 Receptor Is Blocked By Receptor Dimerization. Proc. Natl. Acad. Sci., 97(7):3388-3393.

Vita, C., et al. (1999). Rational Engineering Of A Mini-Protein That Reproduces The Core Of The CD4 Site Interacting With HIV-1 . . . Proc. Natl. Acad. Sci., 96:13091-13096.

Wanda, P.E., and Smith, J.D., (1992). A General Method For Heterokaryon Detection Using Resonance Energy Transfer And A . . . J. Histochem. & Cytochem. 30(12):1297-1300.

Weinhold, K.J., et al. (1989). HIV-1 gp120-Mediated Immune Suppresion And Lymphocyte Destruction In The Absence Of Viral Infection. J. Immunol., 142:3091-3097.

Wells, T.N.C., et al. (1996). Selectivity And Antagonism Of Chemokine Receptors. Journal of Leukocyte Biology, 59:53-60.

Wild, C., et al. (1992). A Synthetic Peptide Inhibitor Of Human Immunodeficiency Virus Replication: Correlation Between Solution . . . Proc. Natl. Acad. Sci., 89:10537-10541.

Wild, C., et al. (1993). A synthetic peptide from HIV-1 Gp41 Is A Potent Inhibitor Of Virus Mediated Cell-Cell Fusion. AIDS Res. Humn. Retroviruses, 9:1051-1053.

Wild, C., et al. (1994). Peptides Corresponding To A Predictive Alpha-Helical Domain Of Human Immunodeficiency Virus Type 1 gp41 Are . . . Proc. Natl. Acad. Sci., 91:9770-9774.

Wild, C., et al. (1995). The Inhibitory Activity Of An HIV Type 1 Peptide Correlates With Its Ability To Interact With A . . . AIDS Res. Hum. Retroviruses, 11:323-325.

Wu, et al. (1997). CCR5 Levels And Expression Pattern Correlate With Infectability By Macrophagetropic HIV-1 In Vitro. J. Exp. Med., 185(9):1681-1691.

Wu, et al. (1997). Interaction Of Chemokine Receptor CCR5 With Its Ligands: Multiple Domains For HIV-1 gp120 Binding And A Single . . . J. Exper. Med., 186(8):1373-1381.

Wu, L., et al. (1996). CD4-Induced Interaction Of Primary HIV-1 gp120 Glycoproteins With The Chemokine Receptor CCR-5. Nature, 384:179-183.

Yamagami, et al. (1994). cDNA Cloning And Fucnctional Expression Of Human Monocyte Chemoattractant Protein 1 Receptor. Biochem. Biophys. Res. Commun., 212:1156-1162.

Yarchoan, et al. (1988). "Clinical Aspects . . . ", in AIDS: Etiology, Diagnosis, . . . , De Vita, et al., eds., Lippincott-Raven Publishers, Philadelphia. pp. 107-109.

Yarchoan, R. and Broder, S. (1992). Correlations Between The In Vitro And The In Vivo Activity Of Anti-HIV Agents: Implications For . . . J. Enzyme Inhibit., 6:99-11.

Ylisastigui, L., et al. (1998). Synthetic Full Length And Truncated RANTES Inhibit HIV-1 Infection Or Primary Macrophages. AIDS, 12:977-984.

Zhang, Y.J., et al. (1994). Structure / Activity Analysis Of Human Monocyte Chemoattractant Protein-1 (MCP-1) Mutagenesis. J. Biol. Chem., 269:15918-15924.

Feb. 15, 1996 advisory Action in connection with U.S. Appl. No. 08/169,311.

Sep. 13, 1995 final Office Action in connection with U.S. Appl. No. 08/169,311.

Nov. 23, 1994 Office Action in connection with U.S. Appl. No. 08/169,311.

Aug. 18, 1994 Office Action in connection with U.S. Appl. No. 08/169,311.

Jul. 16, 1998 Notice of Acceptance in connection with Australian Application No. 14387/95.

Nov. 27 1996 Examiner's First Report in connection with Australian Application No. 14387/95.

Jul. 5, 2000 Notice of Acceptance in connection with Australian Application No. 62690/96.

Nov. 10, 1998 Examiner's First Report in connection with Australian Application No. 62690/96.

Sep. 14, 2006 Official Action in connection with Canadian Application No. 2,224,003.

Sep. 11, 2006 Communication Pursuant to Article 96(2) EPC in connection with European Application No. 96 921 473.3.

Mar. 8, 2006 Summons to Oral Proceedings Pursuant to Rule 71(1) EPC in connection with European Application No. 96 921 473.3.

Feb. 24, 2005 Provision of a Copy of the Minutes in accordance with Rule 76(4) EPC in connection with European Application No. 96 921 473.3.

Feb. 24, 2005 Decision to Refuse a European Patent Application in connection with European Application No. 96 921 473.3.

Aug. 30, 2004 Summons to oral Proceedings Pursuant to Rule 71(1) EPC in connection with European Application No. 96 921 473.3.

Dec. 19, 2002 Communication Pursuant to Article 96(2) EPC in connection with European Application No. 96 921 473.3.

Jul. 6, 2001 Communication Pursuant to Article 96(2) EPC in connection with European Application No. 96 921 473.3.

Dec. 20, 1999 Notice of Allowance and Allowability in connection with U.S. Appl. No. 08/973,601.

Aug. 3, 1999 Advisory Action in connection with U.S. Appl. No. 08/973,601.
Mar. 25, 1999 Office Action in connection with U.S. Appl. No. 08/973,601.
Jun. 24, 1998 Office Action in connection with U.S. Appl. No. 08/973,601.
Jan. 11, 2005 Notice of Allowance and Allowability in connection with U.S. Appl. No. 09/412,284.
Dec. 2, 2003 Final Office Action in connection with U.S. Appl. No. 09/412,284.
Feb. 3, 2003 Office Action in connection with U.S. Appl. No. 09/412,284.
Apr. 8, 2002 Advisory Action in connection with U.S. Appl. No. 09/412,284.
Sep. 11, 2001 Final Office Action in connection with U.S. Appl. No. 09/412,284.
Dec. 19, 2000 Office Action in connection with U.S. Appl. Ser. No. 09/412,284.
Apr. 18, 2007 Office Action in connection with U.S. Appl. No. 11/258,963.
Dec. 26, 2006 Office Action in connection with U.S. Appl. No. 11/258,963.
Feb. 8, 2007 Office Action in connection with U.S. Appl. No. 09/904,356.
May 2, 2006 Final Office Action in connection with U.S. Appl. No. 09/904,356.
Oct. 12, 2005 Office Action in connection with U.S. Appl. No. 09/904,356.
Jul. 29, 2005 Advisory Action in connection with U.S. Appl. No. 09/904,356.
Nov. 17, 2004 Final Office Action in connection with U.S. Appl. No. 09/904,356.
Jul. 1, 2003 Office Action in connection with U.S. Appl. No. 09/904,356.
Sep. 29, 2003 Advisory Action in connection with U.S. Appl. No. 09/118,415.
Jan. 28, 2003 Final Office Action in connection with U.S. Appl. No. 09/118,415.
Apr. 9, 2002 Office Action in connection with U.S. Appl. No. 09/118,415.
Aug. 14, 2001 Advisory Action in connection with U.S. Appl. No. 09/118,415.
Nov. 24, 2000 Final Office Action in connection with U.S. Appl. No. 09/118,415.
Feb. 11, 2000 Office Action in connection with U.S. Appl. No. 09/118,415.
Aug. 3, 2006 Notice of Allowance and Allowability in connection with U.S. Appl. No. 09/891,062.
Jul. 17, 2006 Notice of Allowability in connection with U.S. Appl. No. 09/891,062.
May 18, 2006 Notice of Allowance and Allowability in connection with U.S. Appl. No. 09/891,062.
Aug. 8, 2005 Office Action in connection with U.S. Appl. No. 09/891,062.
Mar. 21, 2004 Office Action in connection with U.S. Appl. No. 09/891,062.
May 28, 2004 Advisory Action in connection with U.S. Appl. No. 09/891,062.
Sep. 24, 2003 Final Office Action in connection with U.S. Appl. No. 09/891,062.
Dec. 18. 2002 Office Action in connection with U.S. Appl. No. 09/891,062.
Apr. 30, 2007 Notice of Allowance and Allowability in connection with U.S. Appl. No. 11/544,346.
Mar. 3, 1997 Office Action in connection with U.S. Appl. No. 08/627,684.
Jun. 23, 1997 Office Action in connection with U.S. Appl. No. 08/663,616.
Mar. 13, 1997 Office Action in connection with U.S. Appl. No. 08/673,682.
Nov. 28, 2000 Notice of Acceptance in connection with Australian Application No. 26074/97.
Jul. 13, 1999 Examiner's First Report in connection with Australian Application No. 26074/97.
Oct. 23, 2006 Official Action in connection with Canadian Application No. 2,250,829.
May 27, 2005 Official Action in connection with Canadian Application No. 2,250,829.
May 4, 2007 Summons to Attend Oral Proceedings Pursuant to Rule 71(1) EPC in connection with European Application No. 97917856.3.
Jan. 27, 2006 Communication Pursuant to Article 96(2) EPC in connection with European Application No. 97917856.3.
Oct. 21, 2005 Communication Pursuant to Article 115(2) EPC in connection with European Application No. 97917856.3.
Apr. 1, 2005 Communication Pursuant to Article 96(2) EPC in connection with European Application No. 97917856.3.
Aug. 5, 2004 Communication Pursuant to Article 96(2) EPC in connection with European Application No. 97917856.3.
Jan. 27, 2004 Communication Pursuant to Article 96(2) EPC in connection with European Application No. 97917856.3.
May. 9, 2003 Communication Pursuant to Article 96(2) EPC in connection with European Application No. 97917856.3.
Mar. 6, 2002 Search Report Communication in connection with European Application No. 97917856.3.
Feb. 27, 2007 Notification of Reasons for Rejection in connection with Japanese Application No. 535610/97 (English translation).
May 19, 2006 Examiner's First Report in connection with Australian Application No. 2004233505.
Jul. 26, 2004 Notice of Acceptance in connection with Australian Application No. 35106/01.
Jul. 5, 2004 Examiner's Second Report in connection with Australian Application No. 35106/01.
Nov. 1, 2002 Examiner's First Report in connection with Australian Application No. 35106/01.
Dec. 4, 2001 Notice of Allowance and Allowability in connection with U.S. Appl. No. 08/831, 823.
Jan. 16, 2001 Notice of Allowance and Allowability in connection with U.S. Appl. No. 08/831,823.
Sep. 26, 2000 Advisory Action in connection with U.S. Appl. No. 08/831,823.
Apr. 11, 2000 Final Office Action in connection with U.S. Appl. No. 08/831,823.
Jul. 21, 1999 Final Office Action in connection with U.S. Appl. No. 08/831,823.
Dec. 21, 1998 Office Action in connection with U.S. Appl. No. 08/831,823.
Aug. 17, 1998 Office Action in connection with U.S. Appl. No. 08/831,823.
Jun. 15, 2006 Final Office Action in connection with U.S. Appl. No. 09/888,938.
Sep. 7, 2005 Office Action in connection with U.S. Appl. No.09/888,938.
Aug. 4, 2004 Office Action in connection with U.S. Appl. No. 09/888,938.
May 5, 2004 Office Action in connection with U.S. Appl. No. 09/888,938.
Jun. 22, 1999 Notice of Allowance and Allowability in connection with U.S. Appl. No. 08/876,078.
Dec. 21, 1998 Final Office Action in connection with U.S. Appl. No. 08/879,078.
Mar. 23, 1998 Office Action in connection with U.S. Appl. No. 08/876,078.
Jun. 16, 2006 Communication Pursuant to Article 96(2) EPC in connection with European Application No. 98 931 261.6.
Jun. 17, 2005 Communication Pursuant to Article 96(2) EPC in connection with European Application No. 98 931 261.6.
Oct. 17, 2006 Final Office Action in connection with U.S. Appl. No. 09/460,216.
Feb. 3, 2006 Office Action in connection with U.S. Appl. No. 09/460,216.
Jul. 29, 2005 Advisory Action in connection with U.S. Appl. No. 09/460,216.
Feb. 9, 2005 Final Office Action in connection with U.S. Appl. No. 09/460,216.

Sep. 26, 2003 Advisory Action in connection with U.S. Appl. No. 09/460,216.
Feb. 27, 2003 Final Office Action in connection with U.S. Appl. No. 09/460,216.
Oct. 2, 2001 Office Action in connection with U.S. Appl. No. 09/460,216.
Sep. 9, 2002 Notice of Acceptance in connection with Australian Application No. 81426/98.
Feb. 27, 2002 Examiner's Second Report in connection with Australian Application No. 81426/98.
Feb. 21, 2001 Examiner's First Report in connection with Australian Application No. 81426/98.
Feb. 4, 1997 Office Action in connection with U.S. Appl. No. 08/665,090.
Aug. 29, 2000 Notice of Allowance and Allowability in connection with 08/874,618.
Nov. 19, 1999 Office Action in connection with U.S. Appl. No. 08/874,618.
May 24, 1999 Final Action in connection with U.S. Appl. No. 08/874,618.
Sep. 2, 1998 Office Action in connection with U.S. Appl. No. 08/874,618.
Dec. 13, 2005 Final Office Action in connection with U.S. Appl. No. 09/724,105.
Mar. 23, 2005 Office Action in connection with U.S. Appl. No. 09/724,105.
Sep. 23, 2004 Office Action in connection with U.S. Appl. No. 09/724,105.
May 19, 2004 Office action in connection with U.S. Appl. No. 09/724,105.
Dec. 19, 2006 Office Action in connection with U.S. Appl. No. 11/400,497.
Aug. 8, 2006 Office Action in connection with U.S. Appl. No. 11/400,497.
May 29, 2001 Notice of Acceptance in connection with Australian Application No. 34026/97.
Sep. 28, 1999 Examiner's First Report in connection with Australian Application No. 34026/97.
Nov. 10, 2006 Official Action in connection with Canadian Application No. 2,257,991.
May 23, 2005 Communications Pursuant to Article 96(2) EPC in connection with European Application No. 97 930 120.7.
Nov. 17, 2004 Communication of partial European search report under Rule 45 EPC in connection with European Application No. 97 930 120.7.
Sep. 9, 2004 Communication of partial European search report under Rule 46(1) EPC in connection with European Application No. 97 930 120.7.
Oct. 17, 2006 Notification of Reasons for Rejection in connection with Japanese Application No. 501895/98 (English translation).
Apr. 5, 2004 Notice of Acceptance in connection with Australian Application No. 21996/00.
Feb. 5, 2003 Examiner's First Report in connection with Australian Application. No. 21996/00.
Mar. 29, 2006 Examiner's First Report in connection with Australian Application No. 20004205164.
Mar. 29, 2006 Examiner's First Report in connection with Australian Application No. 20004205165.
Mar. 1, 2006 communication under Rule 51(4) EPC in connection with European Application No. 99 966 466.7.
Jan. 10, 2005 Communication Pursuant to Article 96(2) EPC in connection with European Application No. 99 966 466.7.
Oct. 14, 2004 Communication Pursuant to Article 96(1) and Rule 51(1) EPC in connection with European Application No. 99 966 466.7.
Jan. 18, 2007 Office communication in connection with Mexican Application No. 1006097.
Oct. 13, 2005 Office communication in connection with Mexican Application No. 1006097.
Feb. 6, 2007 Notice of Allowability in connection with U.S. Appl. No. 09/464,902.
Jan. 8, 2007 Notice of Allowance and Allowability in connection with U.S. Appl. No. 09/464,902.
Apr. 19, 2006 Office Action in connection with U.S. Appl. No. 09/464,902.
Oct. 21, 2005 Office Action in connection with U.S. Appl. No. 09/464,902.
Jun. 15, 2005 Advisory Action in connection with U.S. Appl. No. 09/464,902.
Jan. 13, 2005 Final Office Action in connection with U.S. Appl. No. 09/464,902.
Apr. 2, 2004 Office Action in connection with U.S. Appl. No. 09/464,902.
Oct. 21, 2003 Office Action in connection with U.S. Appl. No. 09/464,902.
Sep. 25, 2001 Office Action in connection with U.S. Appl. No. 09/464,902.
Aug. 7, 2006 Office Action in connection with U.S. Appl. No. 09/594,983.
Mar. 24, 2006 Notice of Allowance and Allowability in connection with U.S. Appl. No. 09/894,983.
Jul. 11, 2005 Final Office Action in connection with U.S. Appl. No. 09/594,983.
Aug. 25, 2004 Office Action in connection with U.S. Appl. No. 09/594,983.
Sep. 23, 2003 Notice of Allowability in connection with U.S. Appl. No. 09/594,983.
Dec. 3, 2002 Final Office Action in connection with U.S. Appl. No. 09/594,983.
Mar. 13, 2002 Office Action in connection with U.S. Appl. No. 09/594,983.
Sep. 28, 2001 Office Action in connection with U.S. Appl. No. 09/594,983.
Dec. 19, 2006 Notice of Allowance and Allowability in connection with U.S. Appl. No. 10/763,545.
Jul. 26, 2006 Office Action in connection with U.S. Appl. No. 10/763,545.
Jun. 13, 2006 Office Action in connection with U.S. Appl. No. 10/763,545.
Feb. 16, 2006 Office Action in connection with U.S. Appl. No. 10/763,545.
Sep. 5, 2006 Communication in connection with U.S. Appl. No. 10/371,483.
Aug. 21, 2006 Communication in connection with U.S. Appl. No. 10/371,483.
May 16, 2006 Notice of Allowance and Allowability in connection with U.S. Appl. No. 10/371,483.
Oct. 24, 2006 Office Action in connection with U.S. Appl. No. 10/371,483.
Jan. 29, 2007 Examiner's First Report in connection Australian Application No. 2003217674.
Feb. 22, 2007 Communication Pursuant to Article 96(2) EPC in connection with European Application No. 03 713 632.2.
Oct. 12, 2004 Communication Pursuant to Rules 109 and 110 EPC in connection with European Application No. 03 713 632.2.
Mar. 14, 2006 Examination Report in connection with New Zealand Application No. 534947.
Feb. 21, 2003 Official Action in connection with Russian Federation Application No. 2004128252/13(030609) (English Translation).
Sep. 29, 2006 Grant of Patent in connection with Singaporean Application No. 200404610-8.
Aug. 7, 2002 Office Action in connection with U.S. Appl. No. 09/663,219.
Jan. 5, 2006 Notice of Allowance and Allowability in connection with U.S. Appl. No. 09/912,824.
Jan. 26, 2005 Final Office Action in connection with U.S. Appl. No. 09/912,824.
Apr. 20, 2004 Office Action in connection with U.S. Appl. No. 09/912,824.
Jul. 2, 2003 Office Action in connection with U.S. Appl. No. 09/912,824.
Jul. 3, 2006 Notice of Acceptance in connection with Australian Appl. No. 2001290925.

Jun. 28, 2005 Examiner's First Report in connection with Australian Application No. 2001290925.

May 24, 2006 Supplementary European search report under Article 157(2) (a) EPC in connection with European Application No. 01970984.9.

Feb. 28, 2005 Formalities Examination in connection with European Application No. 01970984.9.

May 2, 2003 Communication Pursuant to Rules 109 and 110 EPC in connection with European Application No. 01970984.9.

Oct. 25, 2005 Notice of Allowance and Allowability in connection with U.S. Appl. No. 09/828,615.

Sep. 13, 2005 Office Action in connection with U.S. Appl. No. 09/828,615.

Mar. 2, 2005 Office Action in connection with U.S. Appl. No. 09/828,615.

Sep. 17, 2004 Final Office Action in connection with U.S. Appl. No. 09/828,615.

Feb. 23, 2004 Final Office Action in connection with U.S. Appl. No. 09/828,615.

Sep. 9, 2003 Advisory Action in connection with U.S. Appl. No. 09/828,615.

Feb. 21, 2003 Final Office Action in connection with U.S. Appl. No. 09/828,615.

Jun. 25, 2002 Office Action in connection with U.S. Appl. No. 09/828,615.

Jun. 9, 2005 Notice of Allowance and Allowability in connection with U.S. Appl. No. 10/116,797.

Apr. 26, 2005 Final Office Action in connection with U.S. Appl. No. 10/116,797.

Oct. 6, 2004 Office Action in connection with U.S. Appl. No. 10/116,797.

Feb. 9, 2004 Office action in connection with U.S. Appl. No. 10/116,797.

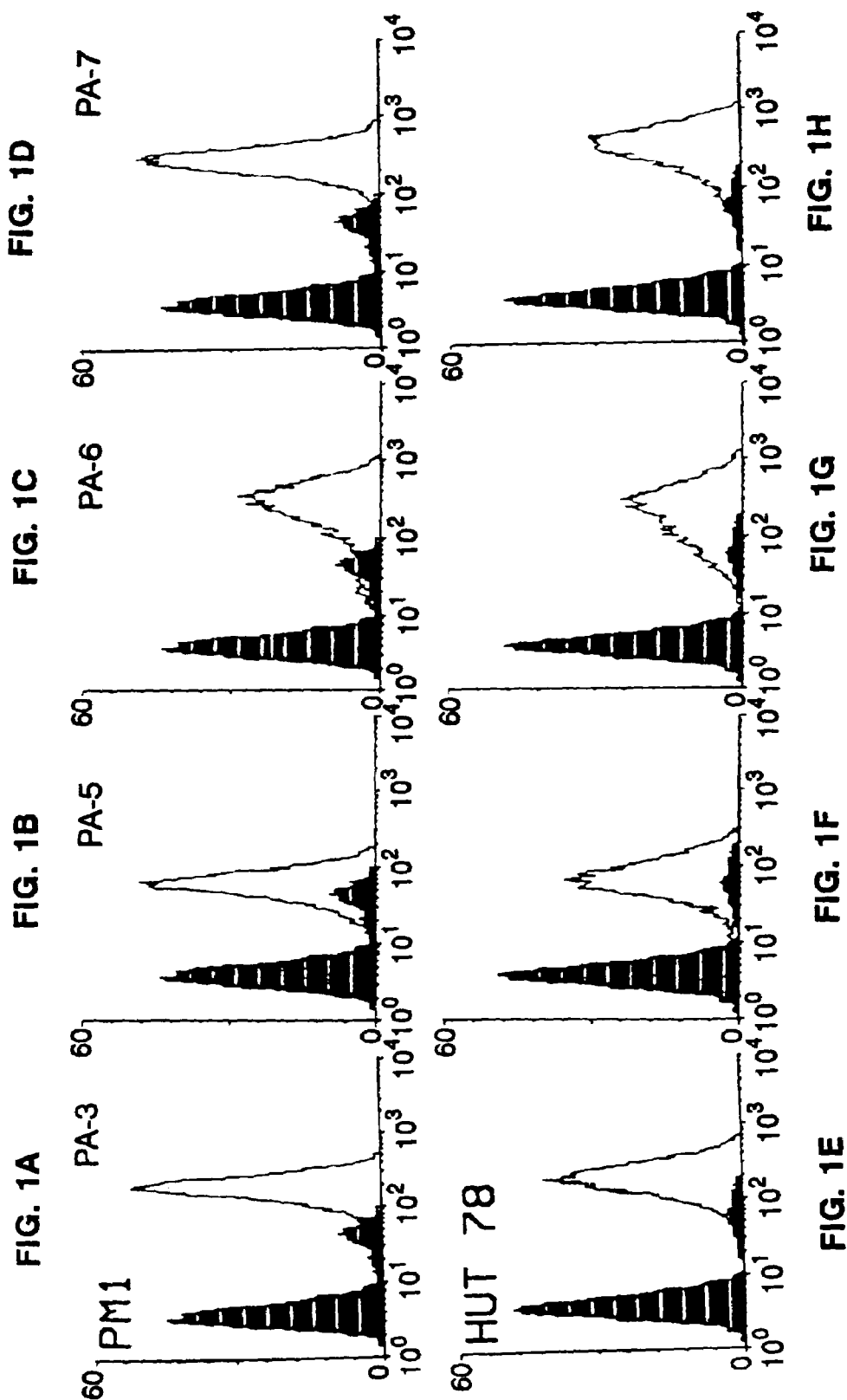

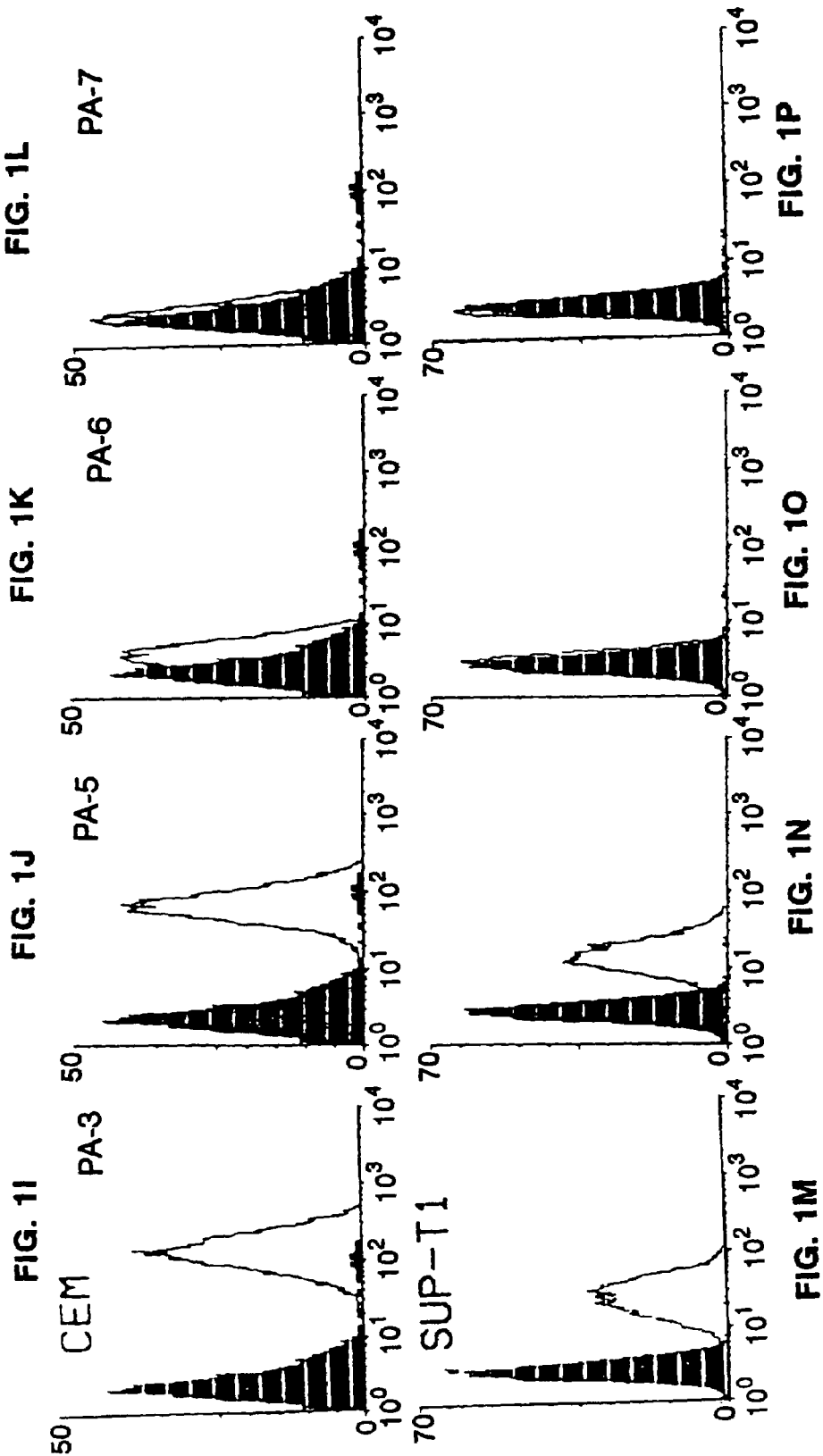

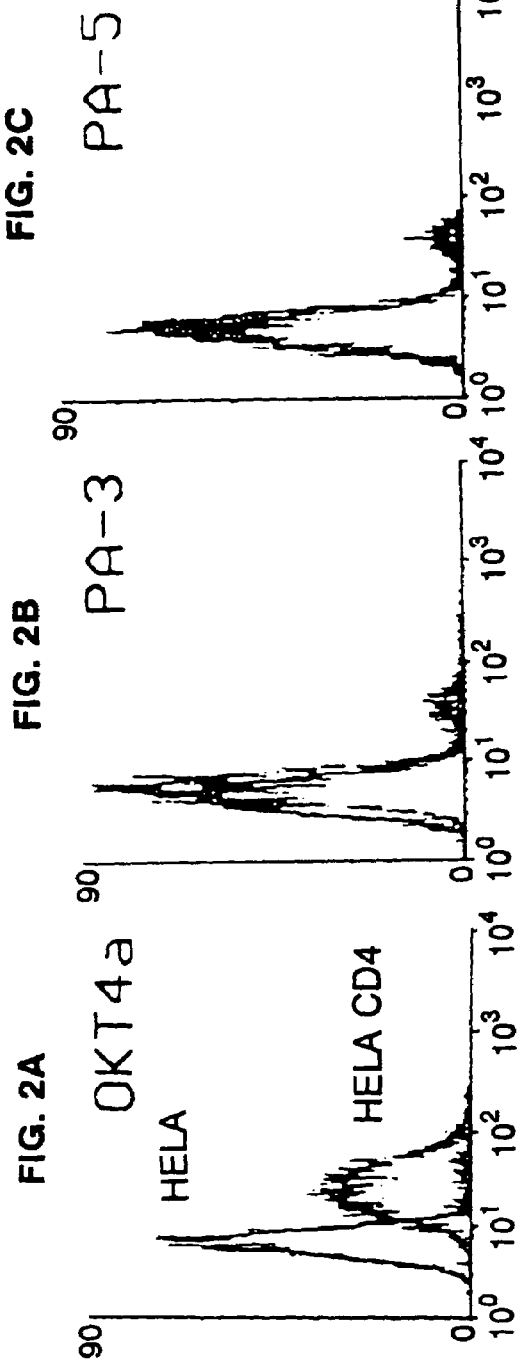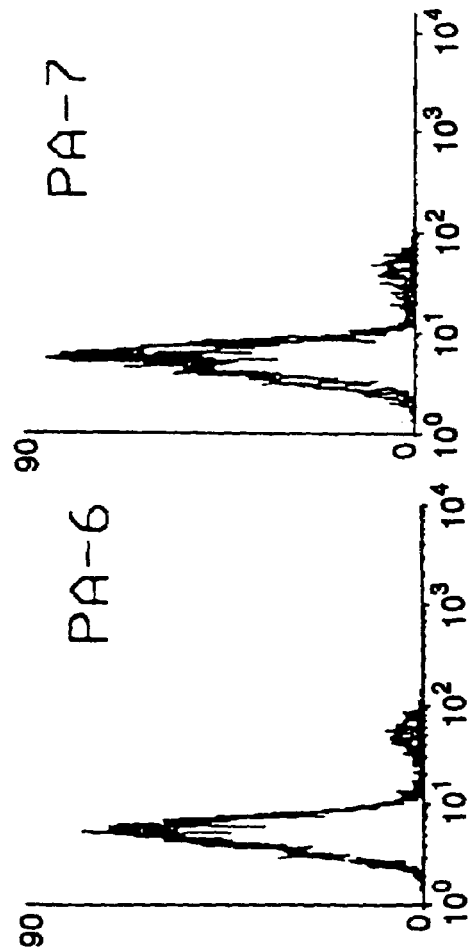

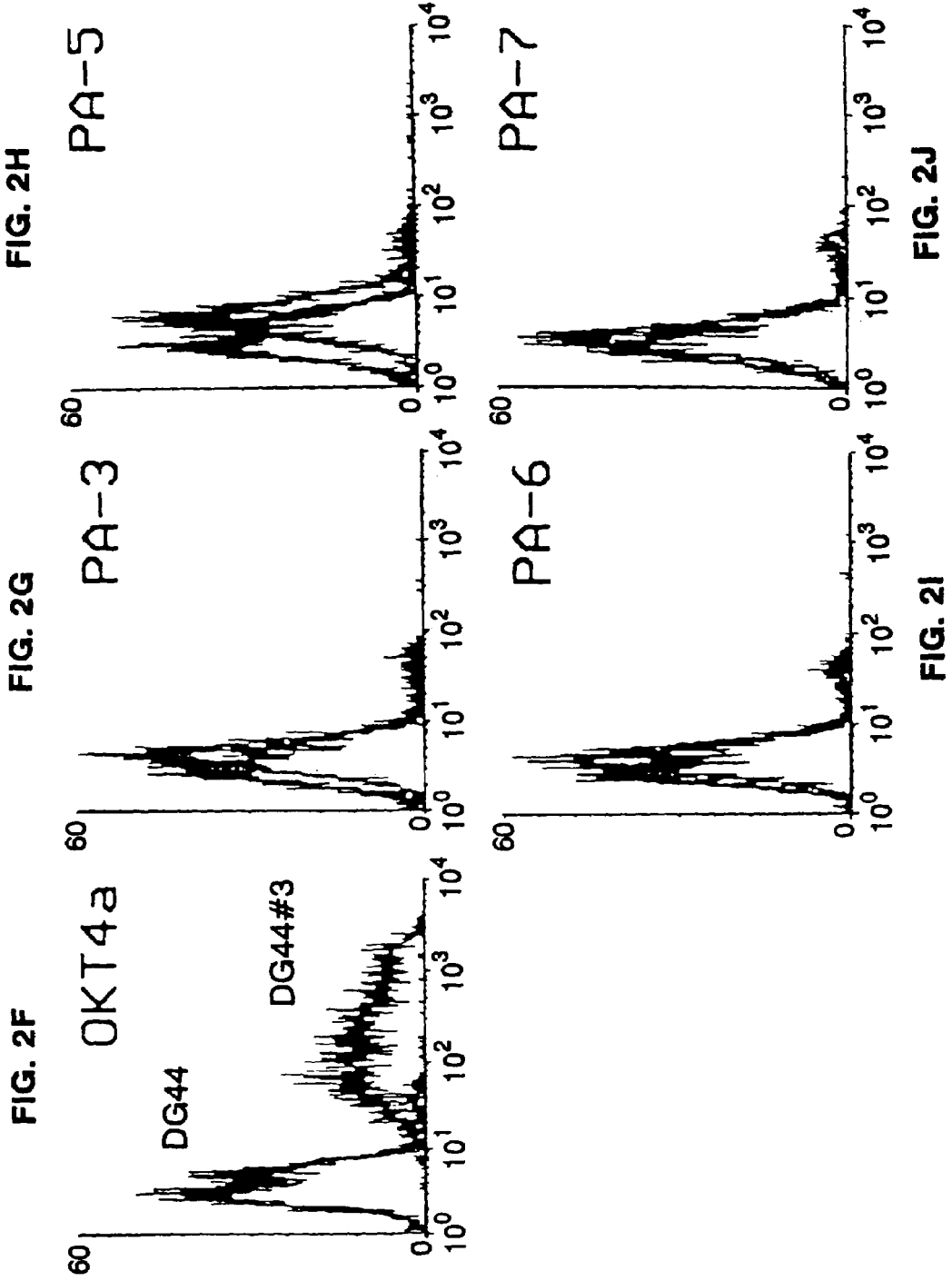

COMPOUNDS CAPABLE OF INHIBITING HIV-1 INFECTION

This application is a continuation of U.S. Ser. No. 11/544,346, filed Oct. 5, 2006, which is a continuation of application U.S. Ser. No. 09/891,062, filed Jun. 25, 2001, now U.S. Pat. No. 7,118,859, which is a continuation of application U.S. Ser. No. 09/118,415, filed Jul. 17, 1998, now abandoned, which is a continuation of PCT International Application No. PCT/US97/00758, filed Jan. 17, 1997, which is a continuation-in-part of application U.S. Ser. No. 08/587,458, filed Jan. 17, 1996, now abandoned, the contents of all of which are incorporated herein by reference into this application.

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

This invention comprises a series of new therapeutics and targets for therapeutic intervention in HIV-1 infection. Monoclonal antibodies have been identified that inhibit HIV-1 envelope-mediated membrane fusion and thereby inhibit virus infection. The antibodies were discovered by screening panels of monoclonal antibodies generated by immunizing mice with human cells. The screening was initially performed using a resonance energy transfer (RET) assay of HIV-1 envelope-mediated membrane fusion. Antibodies which inhibited in this assay were further screened for inhibitory activity in a HIV-1 infection assay.

These inhibitory antibodies act by binding to molecules on the surface of cells, which are required for HIV-1 to fuse with and infect target cells. The molecules are either previously unidentified or their role in HIV-1 entry was previously unrecognized. The cell surface molecules are known as accessory molecules, since they are required for virus entry in addition to the HIV-1 receptor, CD4. While CD4 is required for HIV-1 attachment, the accessory molecules are required for the membrane fusion step of entry. These accessory molecules are generally expressed only on human cells, so HIV-1 does not infect non-human cells that have been engineered to express human CD4 (1,3,8,9). Moreover, several groups have shown that it is possible to complement these non-human CD4$^+$ cells by fusing them (using polyethylene glycol) with CD4$^-$ human cells, resulting in a heterokaryon which is a competent target for HIV-1 envelope-mediated membrane fusion (2,5).

As discussed above, it is generally accepted that accessory molecules are required for HIV-1 fusion. However, the precise nature of these co-receptors or accessory molecules has not yet been discerned. While some cell surface molecules have previously been implicated as fusion accessory molecules (7,10,11), their role has not been confirmed (4).

In some cases, the fusion accessory molecules are found on a subset of human CD4$^+$ cells and are required for infection by HIV-1 isolates with particular tropisms. For example, macrophage-tropic strains of HIV-1 such as HIV-$1_{JR-FL}$ may have different requirements for accessory molecules compared with T lymphotropic strains such as HIV-$1_{LAI}$. This phenomenon is, in part, responsible for differences in tropism between HIV-1 strains.

The current invention includes the monoclonal antibodies and the hybridomas which secret them; also their humanized equivalents, single chain antibodies or antigen binding fragments of the antibodies. These antibodies, single chain antibodies or antibody fragments have value as immunotherapeutics or immunoprophylactics for HIV-1 infection. The invention also includes the genes encoding these antibodies, single chain antibodies and antibody fragments. Moreover, the invention includes the accessory molecules recognized by these monoclonal antibodies, or components of these accessory molecules and region(s) of HIV-1 gp120/gp41 that interact with these accessory molecule(s). In addition the invention includes the genes encoding the accessory molecules. The accessory molecules or their fragments have value as therapeutic or prophylactic agents to inhibit HIV-1 infection. They are also valuable as a basis for rationale drug design to identify inhibitors of HIV-1 infection. This invention provides transgenic animals comprising DNA encoding these accessory molecules or fragments thereof. These transgenic animals are useful as animal models of HIV-1 infection. The invention also includes the use of the antibodies and/or accessory molecules in drug screening assays to identify inhibitors of HIV-1 fusion. Finally, the invention includes the inhibitors identified using these drug screens.

SUMMARY OF THE INVENTION

This invention provides an ant-body capable of specifically inhibiting the fusion of an HIV-1 envelope glycoprotein$^+$ cell with an appropriate CD4$^+$ cell without cross reacting with the HIV-1 envelope glycoprotein or CD4 and capable of inhibiting infection by one or more strains of HIV-1.

This invention also provides a pharmaceutical composition comprising the complete or a portion of the above-described antibody and a pharmaceutically acceptable carrier. This invention provides a method of inhibiting HIV-1 infection in a subject comprising administering an effective amount of the above pharmaceutical composition to the subject.

This invention also provides nucleic acid molecules encoding the complete or a portion of the light chain and the heavy chain protein of the above antibody. This invention also provides vectors comprising these nucleic acid molecules operably linked to a promoter of RNA transcription. This invention also provides host vector systems comprising one or more of these vectors in a suitable host cell.

This invention provides the molecule specifically recognized by the monoclonal antibody capable of specifically inhibiting the fusion of an HIV-1 envelope glycoprotein$^-$ cell with an appropriate CD4$^+$ cell without cross reacting with the HIV-1 envelope glycoprotein or CD4 and which capable of inhibiting infection by one or more strains of HIV-1. In an embodiment, this is a glycolipid molecule. In another embodiment, this is a polypeptide. This invention also provides an isolated nucleic acid molecule encoding the complete or a portion of this polypeptide. In a still further embodiment, the molecule is a multichain polypeptide molecule.

This invention also provides a soluble protein which comprises a portion of the polypeptide or the multichain polypeptide molecule. This invention also provides a pharmaceutical composition comprising an effective amount of the soluble protein to inhibit HIV-1 infection and a pharmaceutically acceptable carrier. This invention also provides a method of inhibiting HIV-1 infection in a subject comprising administering an effective amount of the above pharmaceutical composition to the subject.

This invention provides an isolated nucleic acid molecule encoding the complete or a portion of a polypeptide of the above multichain polypeptide molecule. This invention also provides a vector comprising the nucleic acid molecule encoding the complete or a portion of a polypeptide of the above multichain polypeptide molecule operably linked to a promoter of RNA transcription, and a host vector system comprising this vector in a suitable host cell.

This invention also provides a method for identifying inhibitors of HIV-1 infection comprising steps of: (a) contacting an effective amount of a compound with a system which contains HIV-1 gp120, HIV-1 gp41 or a fragment thereof with the molecule specifically recognized by the monoclonal antibody capable of specifically inhibiting the fusion of an HIV-1 envelope glycoprotein$^+$ cell with an appropriate CD4$^+$ cell without cross reacting with the HIV-1 envelope glycoprotein or CD4 and capable of inhibiting infection by one or more strains of HIV-1 under conditions permitting formation of a complex between HIV-1 gp120, HIV-1 gp41 or a fragment thereof and the molecule, so as to inhibit such formation; and (b) determining the amount of complex formed; and (c) comparing the amount determined in step (b) with the control which is without the addition of the compound, a decrease in the complex formation indicating that the compound is capable of inhibiting HIV-1 infection.

This invention also provides the identified compound and a pharmaceutical composition comprising the identified compound and a pharmaceutically acceptable carrier. This invention provides a method of inhibiting HIV-1 infection in a subject comprising administering an effective amount of this pharmaceutical composition to the subject.

This invention provides a kit for identifying inhibitors of HIV-1 infection which comprises, in separate compartments: (a) purified HIV-1 gp120, HIV-1 gp41 or a fragment thereof; and (b) the molecule specifically recognized by the monoclonal antibody capable of specifically inhibiting the fusion of an HIV-1 envelope glycoprotein$^+$ cell with an appropriate CD4$^+$ cell without cross reacting with the HIV-1 envelope glycoprotein or CD4 and capable of inhibiting infection by one or more strains of HIV-1.

Finally, this invention provides a transgenic nonhuman animal which comprises an isolated DNA molecule encoding the molecule specifically recognized by the monoclonal antibody capable of specifically inhibiting the fusion of an HIV-1 envelope glycoprotein$^+$ cell with an appropriate CD4$^+$ cell without cross reacting with the HIV-1 envelope glycoprotein or CD4 and which inhibits infection by one or more strains of HIV-1. This invention also provides the above-described transgenic nonhuman animal which further comprises a DNA molecule encoding human CD4. This invention further provides different uses of the transgenic animals for screening and development of HIV-1 drugs.

BRIEF DESCRIPTION OF THE FIGURES

FIG. 1. Flow cytometric analysis of human T lymphoblastoid cell lines with mAb PA-3, PA-5, PA-6 and PA-7. Cells were incubated for 15 min at 4° C. with 100 µl of the indicated hybridoma supernatant (open histograms), then washed 3 times in PBS containing 0.05% NaN$_3$. Following a second incubation with FITC-conjugated goat anti-mouse antibody and additional washes the cells were analyzed by flow cytometry. Controls (shaded histograms) were stained with FITC-conjugated goat anti-mouse antibody only. Fluorescence intensity is shown on the X-axis (four decade log scale) and the relative number of cells on the Y-axis. Columns 1-4 are stained with mAb PA-3, PA-5, PA-6 and PA-7, respectively. Rows 1-4 represent the cell lines PM-1, HUT 78, CEM and SUP-T1, respectively.

FIG. 2. Cell surface expression of antigens recognized by the mAb P-3, PA-5, PA-6 and PA-7 on CD4-transfected cell lines and non-transfected counterparts. A comparison of cell surface staining with PA-3, PA-5 and PA-6 and PA-7 was conducted on HeLa or HeLa-CD4 cells (FIGS. 2A-2E) and the Chinese hamster ovary cell line, DG44 or DG44 transfected with human CD4, DG44#3 (FIGS. 2F-2J). The CD4 expression on the transfectants and parental cells was demonstrated by staining with the CD4 specific mAb OKT4A. The histograms showing cell surface staining with monoclonal antibodies PA-3, PA-5, PA-6 and PA-7 on HeLa and HeLa-CD4 overlap, indicating that these antibodies do not recognize human CD4 nor do they recognize any other antigens expressed on the surface of HeLa Cells. Similarly when DG44 and DG44#3 are stained with monoclonal antibodies PA-3, PA-5, PA-6 and PA-7, the histograms overlap, indicating that these monoclonal antibodies do not recognize human CD4 or other surface antigens expressed on the DG44 cells. Although there is a slight increase in binding of PA-5 on the DG44#3 cells compared to the DG44 cells, this is not due to CD4 recognition but rather to non-specific binding. That PA-5 does not recognize human CD4 is confirmed by ELISA assay, staining with HeLa-CD4 cells and immunoprecipitation analysis (see FIG. 3). Staining and Axes are as described in FIG. 1.

DETAILED DESCRIPTION OF THE INVENTION

Figure 3:
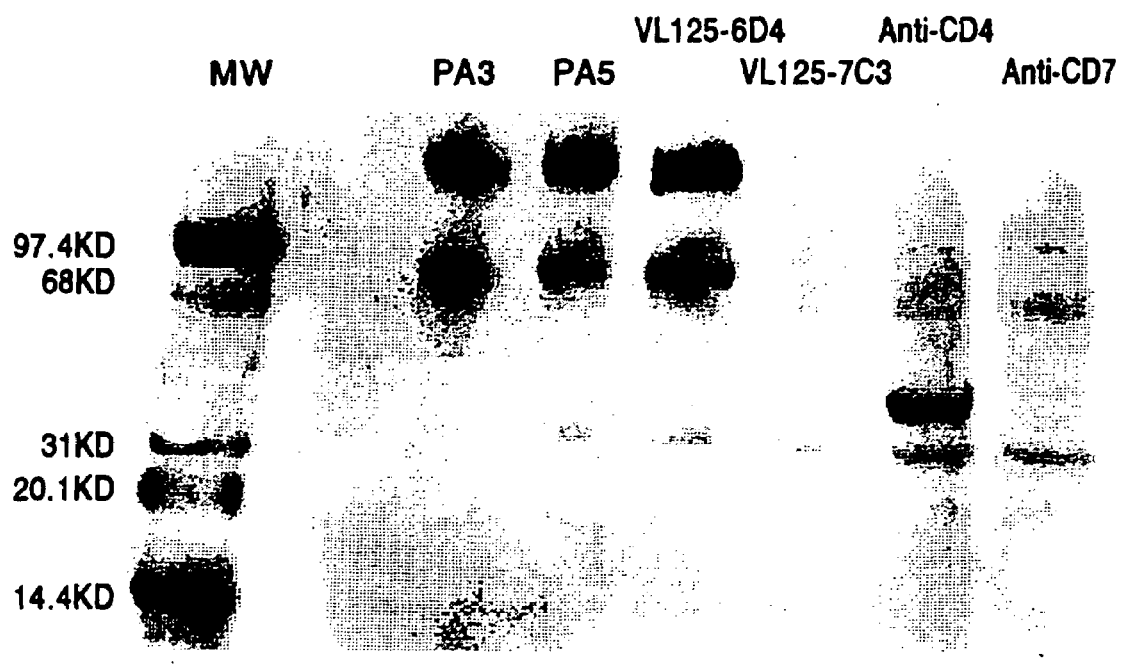
FIG. 3. Monoclonal antibodies PA-3, PA-5, VL125-6D1 recognize the same antigen. PM-1 cells were surface labeled with biotin and immunoprecipitated with hybridoma supernatants PA-3, PA-5, VL125-6D1 and the CD4 specific antibody OKT4A (Ortho Diagnostics, Raritan, N.J.) as described in the experimental methods. Precipitated antigens were resolved on a 4-15% gradient polyacrylamide gel under reducing conditions. Gels were scanned using a Molecular Dynamics (Sunnyvale, Calif.) densitometer. Molecular weight markers are as indicated in the far left lane. Monoclonal antibodies PA-3, PA-5 and VL125-6D1 precipitate two proteins of molecular weights approximately 158 Kd and 87 Kd.

This invention provides an antibody capable of specifically inhibiting the fusion of an HIV-1 envelope glycoprotein$^+$ cell with an appropriate CD4$^+$ cell without cross reacting with the HIV-1 envelope glycoprotein or CD4 and capable of inhibiting infection by one or more strains of HIV-1. In an embodiment, the antibody is a monoclonal antibody. This invention also provides a hybridoma cell line producing the monoclonal antibody.

In another embodiment, the antibody is a chimeric monoclonal antibody. In a separate embodiment, the antibody is a humanized monoclonal antibody. In a still separate embodiment, the antibody is a human monoclonal antibody.

For the purposes of this invention, a "chimeric" monoclonal antibody is a murine monoclonal antibody comprising constant region fragments ($F_c$) from a different species. In a preferred embodiment of this invention, the chimeric monoclonal antibody comprises human $F_c$ and murine $F_{ab}$. For the purposes of this invention, a "humanized" monoclonal antibody is a murine monoclonal antibody in which human protein sequences have been substituted for all the murine protein sequences except for the murine complementarity-determining regions (CDR) of both the light and heavy chains.

This invention also provides single chain antibodies or an antigen binding antibody fragment capable of specifically inhibiting the fusion of an HIV-1 envelope glycoprotein$^+$ cell with an appropriate CD4$^+$ cell without cross reacting with the HIV-1 envelope glycoprotein or CD4 and capable of inhibiting infection by one or more strains of HIV-1. The fragments include but are not limited to Fab and Fab'. The methods to generate the single chain antibodies and antigen binding antibody fragments with particular binding activities are well-known in the art (See for example, Crawley, P (1995) Antibody Patents, in Monoclonal Antibodies: Principles and Applications, Wiley-Liss, Inc. NY, pages 299-335).

This invention also provides a monoclonal antibody capable of competitively inhibiting the binding of the monoclonal antibody capable of specifically inhibiting the fusion of an HIV-1 envelope glycoprotein$^+$ cell with an appropriate CD4$^+$ cell without cross reacting with the HIV-1 envelope glycoprotein or CD4 and capable of inhibiting infection by one or more strains of HIV-1 to its target molecule.

In one embodiment of this invention, the monoclonal antibody is labelled with a detectable marker, for example, a radioactive isotope, enzyme, dye or biotin. This invention provides a pharmaceutical composition comprising the complete or a portion of the monoclonal antibody capable of specifically inhibiting the fusion of an HIV-1 envelope glycoprotein$^+$ cell with an appropriate CD4$^+$ cell without cross reacting with the HIV-1 envelope glycoprotein or CD4 and capable of inhibiting infection by one or more strains of HIV-1 and a pharmaceutically acceptable carrier.

For the purposes of this invention "pharmaceutically acceptable carriers" means any of the standard pharmaceutical carriers. Examples of suitable carriers are well known in the art and may include, but are not limited to, any of the standard pharmaceutical carriers such as phosphate buffered saline solutions, emulsions such as oil/water emulsion, and various type or wetting agents. Other carriers may also include sterile solutions, tablets, coated tablets, and capsules.

Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

The monoclonal antibodies described and claimed herein are useful for isolating the compound to which the monoclonal antibodies bind.

This invention provides a method of inhibiting HIV-1 infection in a subject comprising administering an effective amount of the above-described pharmaceutical composition to the subject.

This invention provides an isolated nucleic acid molecule encoding the complete or a portion of the light chain of the monoclonal antibody. In one embodiment of this invention, the nucleic acid molecule is a DNA molecule. In another embodiment, the DNA molecule is a cDNA molecule. In a separate embodiment, the DNA molecule is a genomic DNA molecule.

This invention provides an isolated nucleic acid molecule encoding the complete or a portion of the heavy chain of the monoclonal antibody. In one embodiment of this invention, the nucleic acid molecule is a DNA molecule. In another embodiment, the DNA molecule is a cDNA molecule. In a separate embodiment, the DNA molecule is a genomic DNA molecule.

This invention provides an isolated nucleic acid molecule encoding the above-described single chain antibody.

The DNA molecules of the subject invention also include DNA molecules coding for polypeptide analogs, fragments or derivatives of polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs wherein one or more amino acid residues is added to a terminal or medial portion of the polypeptides) and which share some or all of the properties of the naturally-occurring forms. These include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The nucleic acid sequences described and claimed herein are useful for generating new viral and circular plasmid vectors described below.

This invention provides the vector, for example a plasmid or a viral vector, comprising a nucleic acid molecule encoding the complete or a portion of light chain protein of the monoclonal antibody operably linked to a promoter of RNA transcription. This invention also provides a vector, for example a plasmid or a viral vector, comprising a nucleic acid molecule encoding the complete or a portion of heavy chain protein of the monoclonal antibody operably linked to a promoter of RNA transcription.

This invention also provides a vector comprising a nucleic acid molecule encoding the above-described single chain antibody operably linked to a promoter of RNA transcription.

This invention also provide a vector comprising the nucleic acid molecules encoding the complete or a portion of light chain protein and the complete or a portion of heavy chain protein of the monoclonal antibody each operably linked to a promoter of RNA transcription.

This invention also provide a host vector system comprising one or more vectors which comprise either the complete or portion of the light chain or a complete or portion of the heavy chain or a combination thereof in a suitable host cell.

This invention further provides the above host vector system, wherein the suitable host cell is selected from a group consisting of a bacterial cell, an insect cell, a yeast cell or a mammalian cell.

This invention provides the molecule specifically recognized by the monoclonal antibody capable of specifically inhibiting the fusion of an HIV-1 envelope glycoprotein$^+$ cell with an appropriate CD4$^+$ cell without cross reacting with the HIV-1 envelope glycoprotein or CD4 and capable of inhibiting infection by one or more strains of HIV-1. In an embodiment, the molecule is a glycolipid. In another embodiment, the molecule is a polypeptide.

This invention also provides an isolated nucleic acid molecule encoding the complete or a portion of the polypeptide which is specifically recognized by the monoclonal antibody capable of specifically inhibiting the fusion of an HIV-1 envelope glycoprotein$^+$ cell with an appropriate CD4$^+$ cell without cross reacting with the HIV-1 envelope glycoprotein or CD4 and capable of inhibiting infection by one or more strains of HIV-1.

This invention provides a multichain polypeptide molecule comprising the polypeptide which is specifically recognized by the monoclonal antibody capable of specifically inhibiting the fusion of an HIV-1 envelope glycoprotein$^+$ cell with an appropriate CD4$^+$ cell without cross reacting with the HIV-1 envelope glycoprotein or CD4 and capable of inhibiting infection by one or more strains of HIV-1.

This invention also provides an isolated nucleic acid molecule encoding the complete or a portion of a polypeptide of the above-described multichain polypeptide molecule. This invention also provides vectors comprising the nucleic acid molecule encoding the complete or a portion of a polypeptide of the above-described multichain polypeptide molecule operably linked to a promoter of RNA transcription. This invention also provides vectors comprising the nucleic acid molecule encoding the complete or a portion of the above polypeptide molecule operably linked to a promoter of RNA transcription.

This invention also provides a host vector system comprising the above vectors in a suitable host cell. The suitable host cell includes but is no limited to a bacterial cell, an insect cell, a yeast cell, a plant cell or a mammalian cell.

The above-described molecules specifically recognized by the antibody may be used to vaccinate healthy subjects for prevention or therapy of HIV infection. These molecules are also useful in identifying specific sites to which these molecules bind on the HIV-1 envelope glycoproteins gp120 and gp41. The sites revealed may be used to generate more specific antibodies directed to these sites. Moreover, this information may be used to design drugs which inhibit the binding of the HIV-1 envelope glycoproteins gp120 or gp41 to the molecule.

This invention also provides a soluble protein which comprises a portion of the polypeptide or the multichain polypeptide molecule.

For the purposes of this invention, a "soluble protein" is a protein free of cell membranes and other cellular components. In one embodiment of this invention, the soluble protein is labelled with a detectable marker, for example, a radioactive isotope, enzyme, dye or biotin. The soluble protein is valuable as a product for making a new and useful pharmaceutical composition.

This invention also provides a pharmaceutical composition comprising an effective amount of the above soluble protein to inhibit HIV-1 infection and a pharmaceutically acceptable carrier.

Methods of determining an "effective amount" are well known to those skilled in the art. Simple titration experiments using different amounts of the soluble protein administered to different animal models of HIV-1 infection or to HIV-1 infected human subjects may be performed to determine such an effective amount. The amount administered to the animal model of HIV-1 infection or HIV-1 infected humans which results in a reduction in HIV-1 infection is an effective amount.

This invention also provides a method of inhibiting HIV-1 infection in a subject comprising administering an effective amount of the pharmaceutical composition of the above soluble protein to the subject.

For the purposes of this invention, "administration" means any of the standard methods of administering a pharmaceutical composition known to those skilled in the art. Examples include, but are not limited to, intravenous, intraperitoneal or intramuscular administration.

This invention provides an isolated nucleic acid molecule encoding the soluble protein. In one embodiment of this invention, the nucleic acid molecule is a DNA molecule. Preferably, the DNA molecule is a cDNA molecule.

The nucleic acid sequences which encode the soluble protein are useful for generating new viral and circular plasmid vectors described below. The nucleic acid molecules are valuable in a new and useful method of gene therapy, i.e., by stably transforming cells isolated from a patient with the nucleic acid molecules and then readministering the stably transformed cells to the patient. Methods of isolating cells include any of the standard methods of withdrawing cells from an animal. Suitable isolated cells include, but are not limited to, bone marrow cells. Methods of readministering cells include any of the standard methods of readministering cells to a patient. U.S. Pat. No. 5,366,346, entitled, "Gene Therapy" describes different gene therapy procedures, the contents of which are incorporated herein by reference.

This invention also provides a vector, for example, a plasmid vector or a viral vector, comprising the isolated nucleic acid molecule operably linked to a promoter of RNA transcription.

The vectors described and claimed herein are valuable as products useful for generating stably transformed eukaryotic host cells, and thereby in new and useful methods of growing such host cells under conditions suitable for the production of the soluble protein.

This invention further provides a host vector system comprising the vector having the sequence which encodes the soluble protein in a suitable host cell. In one embodiment of this invention, the suitable host cell is a stably transformed eukaryotic cell, for example, a stably transformed eukaryotic yeast or mammalian cell. Preferably, the stably transformed cell is a mammalian cell.

The host vector system is valuable as a product useful for the large scale synthesis of the soluble protein by growing the host vector system under conditions suitable for the production of protein and recovering the protein so produced. Thus, a method of producing the soluble protein is also provided. This invention further provides the soluble protein produced by this method.

This invention provides a method for identifying inhibitors of HIV-1 infection comprising steps of: (a) contacting an effective amount of a compound with a system which contains HIV-1 gp120, HIV-1 gp41 or a fragment thereof with the molecule specifically recognized by the monoclonal antibody capable of specifically inhibiting the fusion of an HIV-1 envelope glycoprotein$^+$ cell with an appropriate CD4$^+$ cell without cross reacting with the HIV-1 envelope glycoprotein or CD4 and capable of inhibiting infection by one or more strains of HIV-1 under conditions permitting formation of a complex between the HIV-1 gp120, HIV-1 -gp41 or a fragment thereof with the molecule, so as to inhibit such formation; (b) determining the amount of complex formed; and (c) comparing the amount determined in step (b) with the control which is without the addition of the compound, a decrease in the complex formation indicating that the compound is capable of inhibiting HIV-1 infection. In an embodiment, the compound tested is not previously known. This invention also provide the compound identified by the above method.

This invention also provides a pharmaceutical composition comprising the compound identified by the above method and a pharmaceutically acceptable carrier.

This invention provides a method of inhibiting HIV-1 infection in a subject comprising administering an effective amount of the above pharmaceutical composition comprising the compound identified by the above method to the subject.

This invention provides a kit for identifying inhibitors of HIV-1 infection which comprises, in separate compartments: (a) purified HIV-1 gp120, HIV-1 gp41 or a fragment thereof; and (b) the molecule specifically recognized by the monoclonal antibody capable of specifically inhibiting the fusion of an HIV-1 envelope glycoprotein$^+$ cell with an appropriate CD4$^+$ cell without cross reacting with the HIV-1 envelope glycoprotein or CD4 and capable of inhibiting infection by one or more strains of HIV-1.

This invention provides a transgenic nonhuman mammal which comprises an isolated DNA molecule encoding a molecule specifically recognized by the monoclonal antibody capable of specifically inhibiting the fusion of an HIV-1 envelope glycoprotein$^+$ cell with an appropriate CD4$^+$ cell without cross reacting with the HIV-1 envelope glycoprotein or CD4 and capable of inhibiting infection by one or more strains of HIV-1.

One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding the molecule specifically recognized by the monoclonal antibody capable of specifically inhibiting the fusion of an HIV-1 envelope glycoprotein$^+$ cell with an appropriate CD4$^+$ cell without cross reacting with the HIV-1 envelope glycoprotein or CD4 and capable of inhibiting infection by one or more strains of HIV-1 is purified from a vector by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the transgene.

The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

CD4 may be expressed in the above transgenic animal system such that the animal will be susceptible to HIV-1 infection. Accordingly, this invention also provides the above transgenic nonhuman animals further comprising an isolated DNA molecule encoding the full-length or portion of the CD4 molecule sufficient for binding the HIV-1 envelope glycoprotein. These animal model systems are useful for screening compounds which are capable of inhibiting HIV-1 infection. Moreover, they are useful in predicting or evaluating possible therapeutic applications of HIV drugs. Therefore, this invention also provides a method for screening compounds using these transgenic animals.

This invention will be better understood from the Experimental Details which follow. However, one skilled in the art will readily appreciate that the specific methods and results discussed are merely illustrative of the invention as described more fully in the claims which follow thereafter.

Experimental Details

This invention describes mAb which recognize accessory molecules required for HIV-.1 membrane fusion and tropism. mAb to accessory molecules are first selected by the ability to inhibit HIV-1 envelope glycoprotein-mediated membrane fusion in the RET assay and then analyzed for the ability to inhibit HIV-1 infection in vitro.

Methods

Immunizations and Hybridoma Production.

The immunizing cell line is washed extensively in PBS. Five female six week old Balb/c mice (Charles River Laboratories) are immunized intraperitoneally (IP) with $5 \times 10^6$ cells. Animals receive a minimum of two IP inoculations followed by a three week rest interval. Three days prior to splenectomy one animal receives an intravenous (IV) injection of $0.5 \times 10^6$ cells. The additional animals continue to receive immunizations according to this schedule. Polyethylene glycol (Boehringer Mannheim, Indianapolis, Ind.) is used to fuse murine splenocytes with the murine myeloma cell line Sp2/0 to generate hybridoma cell lines. Hybridomas are plated in 96-well flat bottom tissue culture plates, selected in 1 µg/ml azaserine (Sigma), 5 mM hypoxanthine (Boehringer Mannheim) and 0.8 mM thymidine (Boehringer Mannheim) and maintained in DMEM supplemented with 20% fetal calf serum (FCS), 2 mM L-glutamine, 0.1 mm non-essential amino acids, 1 mM Na pyruvate, 100 U/ml penicillin, 100 µg/ml streptomycin and 10 mM HEPES buffer. When a majority of the hybridomas reach confluency, generally in 10 to 14 days, 100 µl of supernatant are removed and analyzed for the ability to inhibit HIV-1-mediated membrane fusion in the RET assay.

RET Assay.

The RET assay has been adapted to measure HIV-1 envelope glycoprotein-mediated membrane fusion mediated by the laboratory-adapted T cell-tropic strain HIV-1$_{LAI}$ and the macrophage-tropic clinical isolate HIV-1$_{JR-FL}$. HeLa-env$_{LAI}$ cells are able to fuse with a variety of CD4-expressing cells; whereas, HeLa-env$_{JR-FL}$ cells are only able to fuse with PM1 cells, of the panel of cell lines tested.

Briefly, HeLa cells stably expressing HIV-1 gp120/gp41 are labeled with octadecyl fluorescein (F18) and mixed with octadecyl rhodamine (R18) -labeled CD4$^+$ target cells. Membrane fusion of the labeled cells is measured by exciting F18 and measuring emission from R18 (RET) which occurs only when the dyes are closely associated in the same membrane. At the initiation of the RET assay, 100 µl of hybridoma cell supernatant is combined with 2×10$^4$ F18-labeled HeLa-env cells and an equal number of R18-labeled CD4-expressing cells. Results from the RET assay are quantitatively determined using a fluorescence plate reader, data are transferred directly into a spreadsheet and the % RET and % inhibition of RET are automatically calculated. Hybridoma cell supernatants which achieve 50% inhibition or greater in the RET assay are selected for further analysis.

The percent inhibition of RET is defined as follows:

% Inhibition=(Max RET−Exp RET)/(Max RET−Min RET).100 where Max RET is the % RET value obtained at four hours with HeLa-env cells and CD4-expressing cells in the absence of an inhibitory compound; Exp RET is the % RET value obtained for the same cell combination in the presence of an inhibitory compound and Min RET is the background % RET value obtained using HeLa cells in place of HeLa envelope glycoprotein-expressing cells.

Characterization and Purification of the Novel mAb.

The novel mAb generated in this study are characterized. First mAb are tested for reactivity to human CD4. Any mAb found to be specific for human CD4 are not further analyzed and are not considered part of this invention. The hybridoma cell lines which secrete mAb that do not react with CD4 are cloned and used for ascites production, and the mAb are isotyped and purified and tested for ability to inhibit HIV-1 infection.

ELISA Assay for the Detection of CD4-Specific mAb.

Immulon 1 plates (Dynatech Laboratories, Chantilly, Va.) are coated overnight with sCD4 (Progenics) at 120 ng/well in carbonate buffer at pH 9.4 at 4° C. Plates are then washed three times in PTB (PBS containing 0.5% Tween 20, 1% FCS and 0.1% BSA). Following blocking with 5% BSA and three additional washes, plates are incubated for one hour in the presence of 100 µl of hybridoma supernatant or a standard. The anti-CD4 mAb OKT4A is used as the standard and added at concentrations, ranging from 60 ng/ml to 3.25 ng/ml. Plates are washed three times before and after the addition of 100 ng/well of horseradish peroxidase-conjugated goat anti-mouse (Kirkegaard and Perry Laboratories, Gaithersburg, Md.).

O-phenylenediamine (OPD) at 1.2 mg/ml in solution (50 mM Na$_2$HPO$_4$, 25 mM citric acid and 1.2% H$_2$O$_2$) is then added and the plates developed in the dark for. 10-20 min. The reaction is terminated by the addition of 100 µl of 1.3 M H$_2$SO$_4$. The A$_{492}$ is measured on a SLT 400 ATC plate reader (Tecan US, Research Triangle Park, N.C.) and the data analyzed with the winSeLect software program (Tecan).

Cloning Hybridoma Cell Lines by Limiting Dilution.

Hybridoma cell lines are cloned twice by the limiting dilution method. Cells are adjusted in hybridoma culture media to a concentration of five cells per ml by serial dilution. To a 96-well round bottom microliter plate, a volume of 200 µl is pipetted, achieving a density of one cell per well. Supernatants are screened in the RET assay when the cells have reached confluency. Three clones from each of the original cell lines are selected based both on growth rate and the ability to inhibit HIV-1 envelope glycoprotein-mediated membrane fusion and are cryopreserved. The best of the three clones from each group is re-cloned by limiting dilution. Again, the three best clones are cryopreserved. One clone from each of the original hybridomas is selected for ascites production. Prior to ascites production, the isotype of the clones is determined.

Isotype Determination.

The isotype of the monoclonal antibody secreted by each of the twice-cloned hybridoma cell lines is determined using the ImmunoType kit (Sigma). This is an ELISA-based method performed on nitrocellulose strips coated with anti-murine isotype specific antibody.

Ascites Production

For each cloned hybridoma cell line, fifteen female six week old Balb/c mice (Charles River Laboratories) are primed with 0.5 ml of pristane (Sigma). Following a ten day rest period, mice are injected intraperitoneally with 1×10$^6$ hybridoma cells. As ascites fluid accumulates the peritoneal cavity is drained and the fluid collected.

Antibody Purification

Antibody is purified directly from ascites fluid using the protein A-based ImmunoPure Plus purification kit (Pierce, Rockford, Ill.). Ascites fluid is clarified by high speed centrifugation, is diluted and applied to a protein A agarose column. After the column has been extensively washed, antibody is eluted in a high pH buffer. Following neutralization and concentration, the A$_{280}$ is measured and protein concentration determined.

Characterization of the Molecules Recognized by Novel mAb.

The antigens recognized by the novel mAb are characterized. Flow cytometric analysis is conducted in order to evaluate the distribution of antigen expression in hematopoietic cell populations, in cell lines known to be HIV-1 membrane fusion competent or resistant, and in non-primate cell lines. A biochemical analysis of the antigens recognized by the novel mAb is performed. Candidate target epitopes include amino-acid epitopes on proteins, or carbohydrate epitopes on glycoproteins or glycolipids. These possibilities are distinguished by the following analyses. First, antigens are immunoprecipitated from cells in which the surface proteins have been labeled, followed by SDS-PAGE. To determine whether the mAb are recognizing carbohydrate epitopes, cells are treated with neuraminidase prior to FACS analysis and immunoprecipitation. In addition, inhibition of mAb binding to cells by lectins is examined. If these methods indicate the mAb do not recognize proteins but do recognize a carbohydrate epitope, thin layer chromatography is used to determine if the antigens are glycolipids.

Determination of Cellular Distribution of the Molecules by Flow Cytometry.

The distribution of expression of the molecules in peripheral blood mononuclear cell (PBMC) populations is determined. The mononuclear cells are separated from peripheral blood using a Ficoll-Hypaque (Pharmacia) density gradient. PBMC are stained with the hybridoma cell supernatants and antigen expression in the lymphoid and myeloid populations determined by forward and side-scatter gating. The expression of the molecules on various cell lines is compared to the ability of these cell lines to fuse with HIV-1 envelope glycoprotein-expressing cells. The distribution of expression in non-primate cell lines is also evaluated.

Biochemical Analyses

Immunoprecipitation. Immunoprecipitation analysis is used to determine whether proteins are recognized by the novel mAb. A non-radioactive immunodetection with ECL Western blotting (Amersham Life Science, Arlington Heights, Ill.) is used. In this method, cells are labeled with biotin NHS ester. The biotinylated cells are then subjected to lysis and immunoprecipitated with 100 μl of hybridoma supernatant or control mAb. Following SDS-PAGE using 4-15% gradient gels and transfer to nitrocellulose, the immunoprecipitated antigens are visualized using streptavidin-HRP and enhanced chemiluminescence followed by exposure to X-ray film (Kodak). Biotin-labeled cells are lysed in 0.5% NP-40 Lysis Buffer (0.05 M Tris-HCl pH 8.0 containing 0.5% NP-40, 0.15 M NaCl, 0.02% NaN$_3$, 20 KIU/ml aprotinin, 1 mM PMSF). Immune complexes are precipitated with rabbit anti-mouse (Pel-Frez) coated pansorbin (Calbiochem, La Jolla, Calif.). Electrophoresis is performed under reducing and non-reducing conditions to determine if the molecules exist in a monomeric or complexed form. ECL protein molecular weight markers are used to estimate the molecular weights of the molecules.

If immunoprecipitation analysis indicates that the molecules recognized by the novel mAb are proteins, the carbohydrate modifications of these proteins are evaluated. To determine if the proteins contain sialic acid modifications, N-linked oligosaccharides or O-linked oligosaccharides, the immunoprecipitated-antigens are treated with neuraminidase (Sigma), N-glycanase (Boehringer Mannheim) and O-glycanase (Genzyme, Cambridge, Mass.), respectively. A comparison of the mobilities on SDS-PAGE of the enzyme-treated and untreated antigens is made.

Inhibition Analysis of HIV-1 Infection In Vitro Using Novel mAb.

HIV-1 inhibition studies with the mAb are performed with a panel of diverse viruses, including both laboratory-adapted strains and primary isolates. Purified mAb are used in the infection experiments.

HIV-1 In Vitro Infection Assay

Infection studies are performed with both laboratory-adapted stains and primary isolates of HIV-1. Initial experiments are performed with the laboratory adapted strain HIV-1$_{NL4-3}$ and primary isolate HIV-1$_{JR-FL}$. First, the candidate mAb are pre-incubated for 30 min at 37° C. with phytohemagglutinin (PHA)-activated human peripheral blood mononuclear cells (PBMC) prepared from HIV-1 seronegative donors. For each virus strain, an inoculum of approximately 50 TCID-50 is added to 2×10$^6$ PBMC. The cultures are washed three times on day 1, the medium changed on day 4, and the cellular supernatants assayed for p24 core antigen expression using a commercial kit (Abbott Laboratories) on day 7. For each viral strain, the p24 antigen concentrations in the mAb-treated cultures are compared with those of an untreated culture to determine the percentage inhibition of infection. CD4-IgG2, a fusion protein between CD4 and IgG2 which neutralizes all strains of HIV-1, is used as a positive control inhibitor. Initially, three concentrations (50, 25 and 12.5 μg/ml) of the candidate monoclonal antibodies are tested for the ability to inhibit infection by the primary isolate and laboratory-adapted strain of HIV-1. If inhibition is evident, a dose response relationship is determined with serial five-fold dilutions, starting at 50 μg/ml, of the candidate mAb, CD4-IgG2 or other positive or negative control antibodies. A comparison of the p24 antigen concentration in the mAb-treated and untreated cultures is used to determine the percent neutralization, IC$_{50}$ and IC$_{90}$ values by linear regression analysis. The infection experiments are extended to include a larger panel of HIV-1 isolates if promising results are achieved in the preliminary experiments. Alternative target cell lines may be used in place of PBMCs, for example, PM1 cells may be used for HIV-1$_{JR-FL}$, infection experiments.

Experimental Results

The following is a summary of the main experiments pertinent to this invention.

Immunization with HeLa Cells.

Applicants' initial strategy was to immunize with the human carcinoma cell line, HeLa, and screen for monoclonal antibodies (t~) which inhibited HIV-1 envelope glycoprotein-mediated membrane fusion as detected in the RET assay using HeLa-env$_{LAI}$ and HeLa-CD4 cells. Following the first fusion of splenocytes from the HeLa-immunized mice to the murine melanoma fusion partner, SP2/0, hybridoma supernatants were screened in the RET assay but no inhibitory mAb were identified. This scheme was repeated twice more but no inhibitory mAb were identified.

Immunization with C8166 Cells.

The next approach was to use the human CD4$^+$ T lymphoblastoid cell line C8166 for immunization, followed by screening with the RET assay using HeLa-env$_{LAI}$ and HeLa-CD4 cells. This strategy was repeated twice. Several hybridomas were identified which secreted mAb inhibiting HIV-1 envelope glycoprotein-mediated membrane fusion during the course of this analysis. All of these were later identified as CD4-specific mAb and thus are not included as part of this invention. However, this work did provide evidence that it is possible to produce mAb to cell surface molecules which inhibit fusion in the RET assay.

Immunization with Protease-Digested Human Erythrocytes.

The third strategy involved immunization with proteinase K digested human erythrocytes and screening with the RET assay using HeLa-env$_{LAI}$ and HeLa-CD4 cells. This approach was used following a published study which had found that when human erythrocytes were fused to mouse CD4$^+$ cells using polyethylene glycol, the heterokaryons became competent targets for HIV-1 envelope-mediated membrane fusion, suggesting that erythrocyte membranes contain fusion accessory molecules (6). Moreover, proteinase K treatment of the erythrocytes did not abrogate this complementation. Following immunization with proteinase K digested erythrocytes, applicants selected several hybridomas which inhibited in the RET assay using HeLa-env$_{LAI}$ and HeLa-CD4 cells. Unfortunately, the hybridomas were unstable and thus failed to inhibit in subsequent RET assays.

Immunization with PM1 Cells.

HeLa cells (HeLa-env$_{JR-FL}$) which stably express the envelope glycoprotein from the JR-FL strain of HIV-1 were generated. The RET assay was then adapted to measure the fusion of HeLa-env$_{JR-FL}$ with PM1 cells. PM1 cells were then used for immunizations. The resulting hybridomas were screened in the RET assay using HeLa-env$_{JR-FL}$ and PM1 cells. Several hybridomas which inhibited fusion by 50% or greater were selected for further analysis. Hybridomas were analyzed by RET assay, flow cytometry and ELISA assay. All of the hybridomas selected for further analysis secreted mAb which continue to inhibit in the RET assay using HeLa-env$_{JR\text{-}FL}$ and PM1 cells. Four of these hybridomas designated PA-3, PA-5, PA-6 and PA-7, have been cloned twice by the limiting dilution method and ascites fluid has been produced. mAb are currently being purified from the ascites fluid.

Inhibition of HIV-1 Envelope Glycoprotein-Mediated Membrane Fusion in the RET Assay by Anti-PM1 Hybridoma Supernatants.

In addition to inhibiting in the RET assay using HeLa-env$_{JR\text{-}FL}$ and PM1 cells, the culture supernatants from PA-3, PA-5, PA-6 and PA-7 also inhibit in the RET assay using HeLa-env$_{LAI}$ cells and certain CD4$^+$ target cells (Table 1). HIV-1$_{LAI}$ envelope glycoprotein-mediated membrane fusion with PM-1, and HUT-78 was inhibited by all of the mAb secreted from these hybridoma cell lines. Whereas, fusion between HeLa-env$_{LAI}$ and CEM was inhibited by PA-3 and PA-5 but less so by PA-6 or PA-7. The fusion between HeLa-env$_{LAI}$ and C8166 or Sup-T1 cells was inhibited minimally or not at all by these mAb.

TABLE 1

Inhibition of HIV-1 envelope glycoprotein mediated cell fusion by novel mAb.

| Envelope expressing cells | CD4+ cells | % RET | % Inhibition of RET by novel mAb | | | |
|---|---|---|---|---|---|---|
| | | | PA-3 | PA-5 | PA-6 | PA-7 |
| HeLa-env$_{JR\text{-}FL}$ | PM-1 | 16.3 | 85.3 | 96.3 | 92 | 67 |
| HeLa-env$_{LAI}$ | PM-1 | 12.4 | 89.7 | 100 | 81 | 69 |
| HeLa-env$_{LAI}$ | HUT-78 | 10.9 | 51.3 | 60.3 | 55.7 | 52.7 |
| HeLa-env$_{LAI}$ | CEM | 9.5 | 71.8 | 68 | 33 | 21 |
| HeLa-env$_{LAI}$ | HeLa-CD4 | 11.4 | 0 | 0 | 7.7 | 0 |
| HeLa-env$_{LAI}$ | SUP-T1 | 19.8 | 2.5 | 0 | 18 | 11 |
| HeLa-env$_{LAI}$ | C8166 | 15.4 | 9.7 | 22 | 22.3 | 13 |

Distribution of Expression of Antigens Recognized by mAb PA-3, PA-5, PA-6 and PA-7.

The surface expression of the antigens recognized by the mAb PA-3, PA-5, PA-6 and PA-7 on cell lines known to fuse with HeLa-env$_{LAI}$ or HeLa-env$_{JR\text{-}FL}$ was evaluated by flow cytometry (FIG. 1). All of the mAb recognize molecules present on the plasma membrane of PM1 and the related cell line HUT-78. Antigen expression on these two cell lines was equivalent. PA-3 and PA-5 recognize cell surface antigens on both CEM and Sup-T1 cells. Paradoxically, while fusion between HeLa-env$_{LAI}$ and CEM cells was inhibited by these mAb, fusion between HeLa-env$_{LAI}$ and SUP-T1 was not. Neither PA-6 nor PA-7 recognized CEM or SUP-T1 or significantly inhibited fusion of HeLa-env$_{LAI}$ with CEM or Sup-T1. Likewise none of the four novel mAb recognized cell surface antigens on HeLa cells or significantly inhibited HeLa-CD4 fusion with HeLa-env$_{LAI}$.

A comparison of cell surface staining of two CD4 transfected cell lines and their non-transfected counterparts with mAb PA-3, PA-5, PA-6 and PA-7 (FIG. 2) showed that there was no significant increase in expression on the CD4-transfectants. This data is in complete agreement with ELISA data indicating that none of these four mAb were reactive with human CD4.

Biochemical Analysis of Cell Surface Antigens Recognized by mAb PA-3, PA-5, PA-6 and PA-7.

Figure 4:
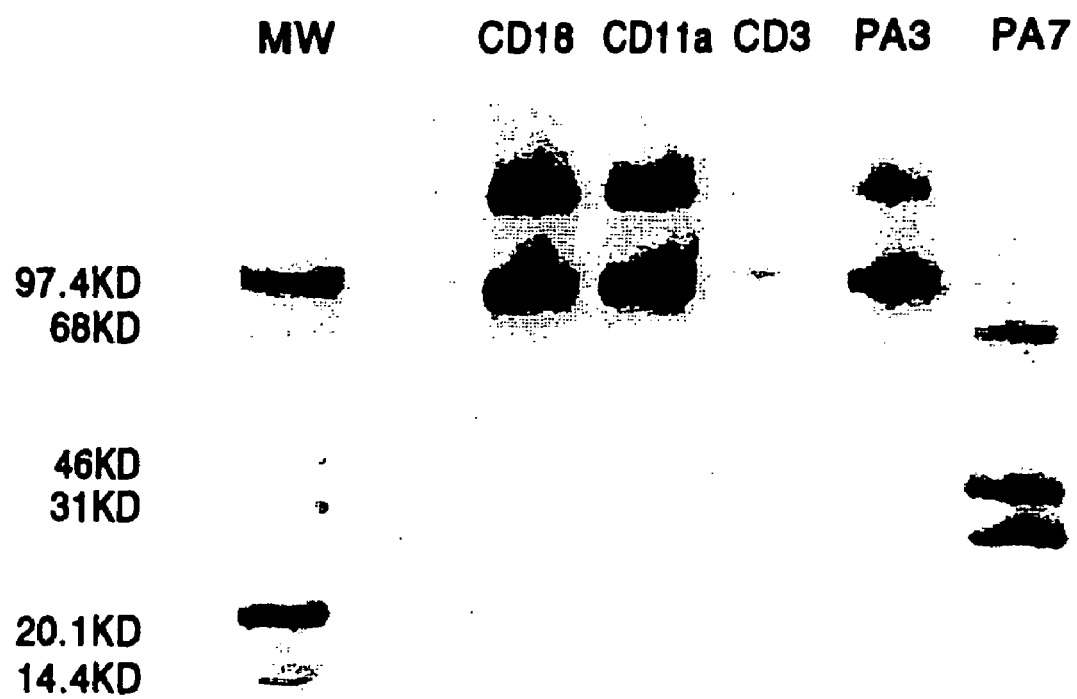
FIG. 4. Antigens recognized by PA-3 but not PA-7 co-migrate with LFA-1 (CD11a/CD18). PM-1 cells were surface labeled with biotrn and immunoprecipitated with hybridoma supernatants S PA-3 and PA-7 and the CD3 specific UCHT1 (Pharmingen, San Diego, Calif.), the CD11a specific 25.3.1(Immunotech, Westbrook, Me.) and the CD18 specific 7E4 (Immunotech) as described in the experimental methods. Precipitated antigens were resolved on a 4-15% gradient polyacrylamide gel under reducing conditions. Gels were scanned using a Molecular Dynamics (Sunnyvale, Calif.) densitometer. Antigens precipitated by PA-3 but not PA-7 co-migrate with those precipitated by 25.3.1 and 7E4. Antigens recognized by UCHTI did not resolve on this gel. Molecular weight markers are as indicated in the far left lane.

The mAb PA-3, PA-5, PA-6 and PA-7 were used to immunoprecipitate cell surface antigens from PM1 cells by the method described above. This analysis revealed that PA-3 and PA-5 recognized the same antigen (FIG. 3). Whether or not both mAb recognized the same epitope remains to be determined. Two bands of approximate molecular weight 158 Kd and 87 Kd are precipitated with these mAb. When mAb directed against the two chains of LFA-1 (CD11a and CD18) are run along side immunoprecipitations with PA-3, bands of similar size are precipitated (FIG. 4). Thus it is highly likely that PA-3 and PA-5 recognize either CD11a or CD18.

Figure 5:
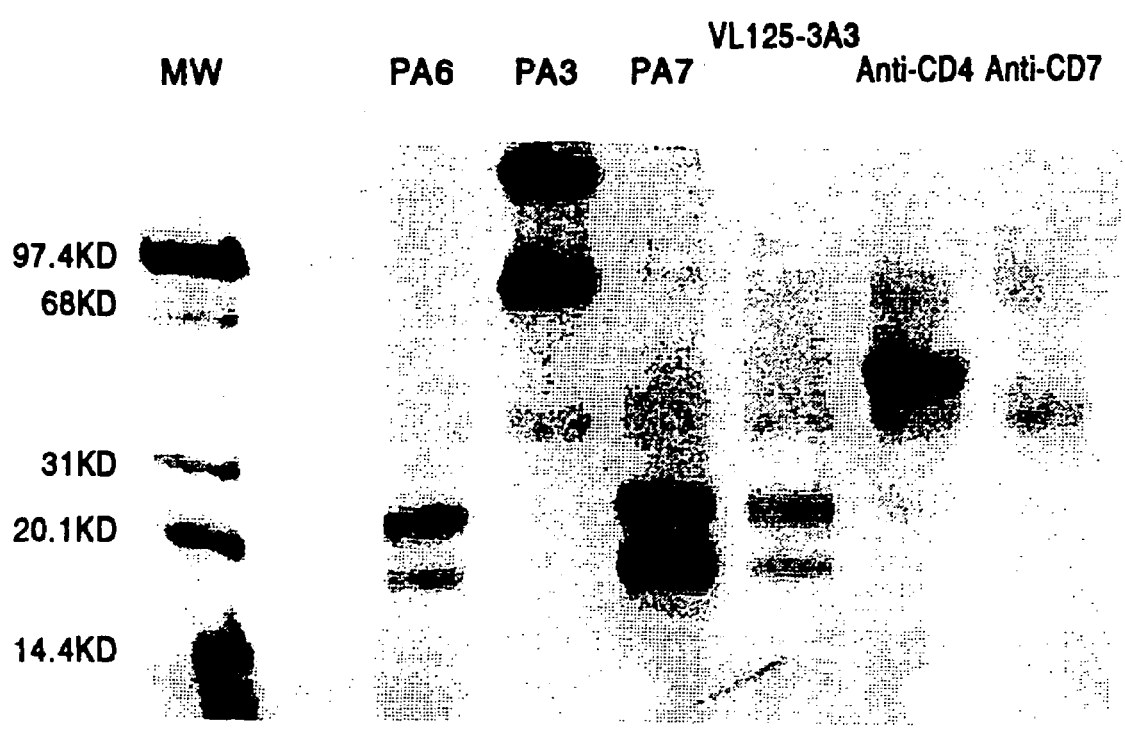
FIG. 5. Monoclonal antibodies PA-6 and PA-7 recognize the same antigen. PM-1 cells were surface labeled with biotin and immunoprecipitated with hybridoma supernatants PA-3, PA-6, PA-7 and the CD4 specific antibody OKT4A Ortho Diagnostics) as described in the experimental methods. Precipitated antigens were resolved on a 4-15% gradient polyacrylamide gel under reducing conditions Gels were scanned using a Molecular Dynamics (Sunnyvale, Calif.) densitometer molecular weight marker are as indicated in the far left lane. Monoclonal antibodies PA-6 and PA-7, precipitate two proteins of molecular weights approximately 24.8 Kd and 19.1 Kd.
Figure 6:
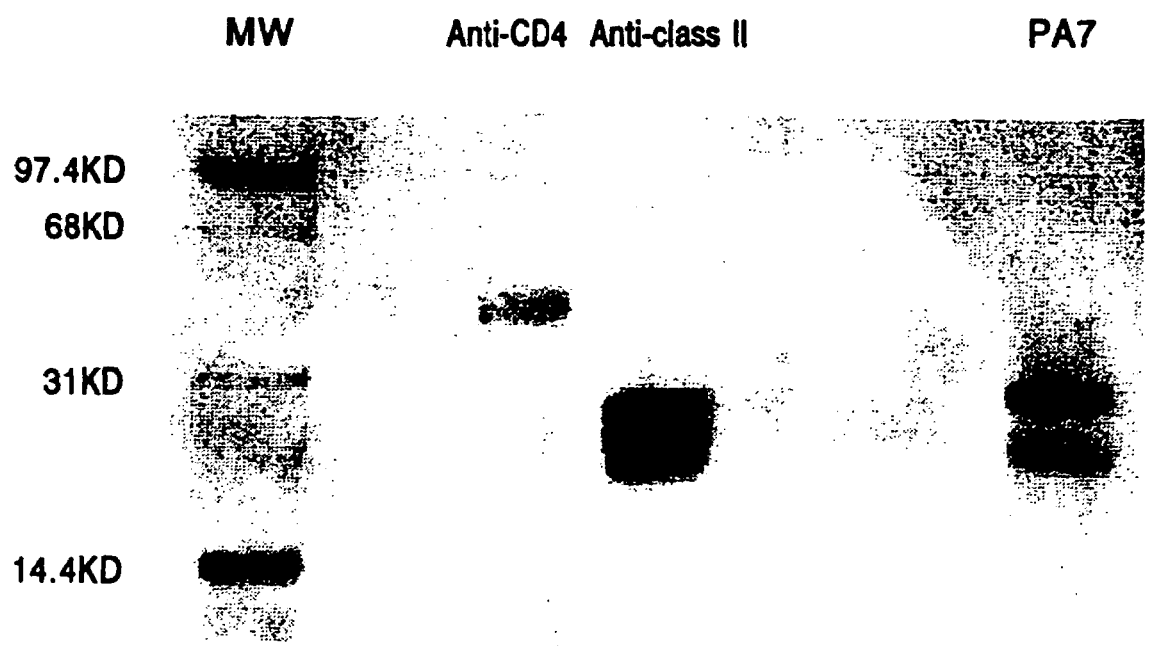
FIG. 6. Antigens recognized by PA-7 co-migrate with HLA class II. PM-1 cells were surface labeled with biotin and immunoprecipitated with hybridoma supernatants PA-7 and the CD4 specific OKT4A (Ortho) and the HLA class II specific TU39 (Pharmingen) as described in the methods section. Precipitated antigens were resolved on a 4-15% gradient polyacrylamide gel under reducing conditions. Antigens precipitated by PA-7 appear to co-migrate with those precipitated by TU39. Molecular weight markers are as indicated in the far left lane.

PA-6 and PA-7 both precipitate two proteins of molecular weights approximately 24.8 Kd and 19.1 Kd and thus appear to recognize the same antigen (FIG. 5). However it is unclear whether they recognize the same epitope. When a pan specific HLA class II. mAb is used for immunoprecipitation, bands of similar mobilities to those precipitated with PA-6 and PA-7 are resolved (FIG. 6). Thus PA-6 and PA-7 may recognize HLA class II.

Inhibition of HIV-1$_{NL4\text{-}3}$ and HIV-1$_{JR\text{-}FL}$ Infection by PA-3, PA-5 and CD4-IgG2.

The assay method was described above. Experiments demonstrated that the antibodies PA-3 and PA-5 inhibit infection by both the laboratory-adapted isolate HIV-1$_{NL4\text{-}3}$ and the primary macrophage-tropic isolate HIV-1$_{JR\text{-}FL}$. Inhibition in these assays was dose-dependent as shown in the following Table 2:

TABLE 2

Inhibition of HIV-1$_{NL4\text{-}3}$ and HIV-1$_{JR\text{-}FL}$ infection by PA-3, PA-5 and CD4-IgG2.

| Concentration µg/ml | PA-3 % Inhibition of | | PA-5 % Inhibition of | | CD4-IgG2* % Inhibition of | |
|---|---|---|---|---|---|---|
| | HIV-1$_{NL4\text{-}3}$ | HIV-1$_{JR\text{-}FL}$ | HIV-1$_{NL4\text{-}3}$ | HIV-1$_{JR\text{-}FL}$ | HIV-1$_{NL4\text{-}3}$ | HIV-1$_{JR\text{-}FL}$ |
| 50.0 | 90.8 | 69.5 | 75.8 | 57.4 | 100.0 | 95.3 |
| 25.0 | 72.2 | 49.1 | 62.0 | 44.6 | 99.4 | 75.1 |
| 12.5 | 61.8 | 33.9 | 58.9 | 35.4 | 77.7 | 62.2 |

*Positive control CD4-IgG2 is a fusion protein between CD4 and human IgG2 which neutralizes all strains of HIV-1.

REFERENCES

1. Ashorn P A., Berger E A., and Moss B. 1990. Human immunodeficiency virus envelope glycoprotein/CD4-mediated fusion of nonprimate cells with human cells. J. Virol. 64:2149-2156.
2. Broder C C., Dimitrov D S., Blumenthal R., and Berger E A. 1993. The block to HIV-1 envelope glycoprotein-mediated membrane fusion in animal cells expressing human CD4 can be overcome by a human cell component(s). Virology 193:483-491.
3. Clapham P R., Blanc D., and Weiss R A. 1991. Specdfic cell surface requirements for the infection of CD4-positive cells by human immunodeficiency virus types 1 and 2 and by simian immunodeficiency virus. Virology 181: 703-715.
4. Dalgleish A G. 1995. HIV and CD26. Nature Medicine 1:881-882.
5. Dragic T., Charneau P., Clavel F., and Alizon M. 1992. Complementation of murine cells for human immunodeficiency virus envelope/CD4-mediated fusion in human/murine heterokaryons. J. Virol. 66:4794-4802.
6. Dragic T., Picard L., and Alizon M. 1995. Proteinase-resistant factors in human erythrocyte membranes mediate CD4-dependent fusion with cells expressing human immunodeficiency virus type 1 envelope glycoproteins. J. Virol. 69:1013-1018.
7. Golding H., Dimitrov D S., and Blumenthal R. 1992. LFA-1 adhesion molecules are not involved in the early stages of HIV-1 env-mediated cell membrane fusion. AIDS Res Hum Retroviruses 8:1593-1598.
8. Harrington R D. and Geballe A P. 1993. Cofactor requirement for human immunodeficiency virus type 1 entry into a CD4-expressing human cell line. J. Virol. 67:5939-5947.
9. Maddon P J., Dalgleish A G., McDougal J S., Clapham P R., Weiss R A., and Axel R. 1986. The T4 gene encodes the AIDS virus receptor and is expressed in the immune system and the brain. Cell 47:333-348.
10. Sato A I., Balamuth F B., Ugen K E., Williams W V., and Weiner D B. 1994. Identification of CD7 glycoprotein as an accessory molecule in HIV-1-mediated syncytium formation and cell free infection. J. Immunol. 152:5142-5152.
11. Sommerfelt M A. and Asjo B. 1995. Intercellular adhesion molecule 3, a candidate human immunodeficiency virus type 1 co-receptor on lymphoid and monocytoid cells. J. Gen. Virol. 76:1345-1352.

What is claimed is:

1. A monoclonal antibody or a portion of such monoclonal antibody effective to (a) specifically inhibit 67% or greater of fusion of a CD4+ PM-1 cell to a HeLa cell expressing envelope glycoprotein from HIV-1$_{JR-FL}$, and (b) inhibit 18% or less of fusion of a CD4+ SUP-T1 cell to a HeLa cell expressing envelope protein from HIV-1$_{LAI}$, wherein the antibody (i) does not crossreact with HIV-1 envelope glycoprotein or CD4, (ii) reacts with an antigen on the surface of a PM-1 cell having an approximate molecular weight of 44 kD, (iii) does not react with an antigen on the surface of a SUP-T1 cell, and (iv) is at least as active as monoclonal antibody PA-7 produced by the hybridoma designated PA-7 (ATCC Accession No. PTA-6638) in inhibiting fusion as recited in (a) above and less active than inonoclonal antibody PA-6 produced by the hybridoma designated PA-6 (ATCC Accession No. PTA-6637) in inhibiting fusion as recited in (b) above.

2. The monoclonal antibody of claim 1, wherein the monoclonal antibody is a chimeric monoclonal antibody.

3. The monoclonal antibody of claim 1, wherein the monoclonal antibody is a humanized monoclonal antibody.

4. The monoclonal antibody of claim 1, wherein the monoclonal antibody is a human monoclonal antibody.

5. The monoclonal antibody of claim 1, wherein the portion of the monoclonal antibody is a single chain antibody or an antigen binding fragment.

6. The monoclonal antibody of claim 1 or the portion of such monoclonal antibody, wherein the monoclonal antibody or the portion of such monoclonal antibody is labeled with a detectable marker.

7. The monoclonal antibody of claim 6 or the portion of such monoclonal antibody, wherein the detectable marker is a radioactive isotope, an enzyme, a dye or biotin.

* * * * *